United States Patent
Courvoisier et al.

(10) Patent No.: US 8,318,979 B2
(45) Date of Patent: Nov. 27, 2012

(54) PROCESS FOR ENANTIOSELECTIVE SYNTHESIS OF SINGLE ENANTIOMERS OF MODAFINIL BY ASYMMETRIC OXIDATION

(75) Inventors: Laurent Courvoisier, Thorndale, PA (US); Veronique Courvoisier, legal representative, Thorndale, PA (US); Gerard Duret, Boulogne (FR); Stephanie Graf, Belloy en France (FR); Laurence Prat-Lacondemine, Pontault Combault (FR); Francois Rebiere, Antony (FR); Nicolas Sabourault, Paris (FR)

(73) Assignee: Cephalon France, Maisons-Alfort (FR)

( * ) Notice: Subject to any disclaimer, the term of this patent is extended or adjusted under 35 U.S.C. 154(b) by 0 days.

(21) Appl. No.: 13/070,703

(22) Filed: Mar. 24, 2011
(Under 37 CFR 1.47)

(65) Prior Publication Data

US 2012/0123161 A1    May 17, 2012

Related U.S. Application Data

(63) Continuation of application No. 12/050,666, filed on Mar. 18, 2008, now Pat. No. 7,915,449, which is a continuation of application No. 11/082,530, filed on Mar. 17, 2005, now Pat. No. 7,368,591, which is a continuation-in-part of application No. 10/943,360, filed on Sep. 17, 2004, now Pat. No. 7,317,126.

(60) Provisional application No. 60/507,089, filed on Oct. 1, 2003.

(30) Foreign Application Priority Data

Sep. 19, 2003 (EP) .................... 03292312

(51) Int. Cl.
*C07C 321/00* (2006.01)
(52) U.S. Cl. ..................................... 564/162
(58) Field of Classification Search .................. 564/162
See application file for complete search history.

(56) References Cited

U.S. PATENT DOCUMENTS

| | | | |
|---|---|---|---|
| 4,098,824 A | 7/1978 | Lafon | |
| 4,177,290 A | 12/1979 | Lafon | |
| 4,927,855 A | 5/1990 | Lafon | |
| 5,180,745 A | 1/1993 | Lafon | |
| 5,391,576 A | 2/1995 | Lafon | |
| 5,401,776 A | 3/1995 | Laurent | |
| 5,612,379 A | 3/1997 | Laurent | |
| 5,719,168 A | 2/1998 | Laurent | |
| RE37,516 E | 1/2002 | Grebow et al. | |
| 6,489,363 B2 | 12/2002 | Jacobs et al. | |
| 6,849,120 B2 | 2/2005 | Singer et al. | |
| 6,875,893 B2 | 4/2005 | Largeau et al. | |
| 6,919,378 B2 | 7/2005 | Jacobs et al. | |
| 6,992,219 B2 | 1/2006 | Broquaire et al. | |
| 7,317,126 B2 | 1/2008 | Rebiere et al. | |
| 7,368,591 B2 | 5/2008 | Rebiere et al. | |
| 7,915,449 B2 * | 3/2011 | Rebiere et al. ................. | 564/162 |
| 2002/0043207 A1 | 4/2002 | Singer et al. | |
| 2002/0099097 A1 | 7/2002 | Jacobs et al. | |
| 2003/0022940 A1 | 1/2003 | Corvari et al. | |
| 2003/0077297 A1 | 4/2003 | Chen et al. | |
| 2003/0114470 A1 | 6/2003 | Wizel et al. | |
| 2003/0180352 A1 | 9/2003 | Patel et al. | |

(Continued)

FOREIGN PATENT DOCUMENTS

CA    1 199 916    1/1986

(Continued)

OTHER PUBLICATIONS

Abushanab, E., et al., "Stereospecific microbial oxidation of thioethers to sulfoxides. Application to the synthesis of R-mevalonolactone," *Tetrahedron Letts.*, 1978, 37, 3415-3418.

(Continued)

*Primary Examiner* — Rei-tsang Shiao

(57) ABSTRACT

The invention relates to a method for preparing a sulphoxide compound of formula (I) either as a single enantiomer or in an enantiomerically enriched form, comprising the steps of:
  a) contacting a pro-chiral sulphide of formula (II) with a metal chiral complex, a base and an oxidizing agent in an organic solvent; and optionally
  b) isolating the obtained sulphoxide of formula (I).

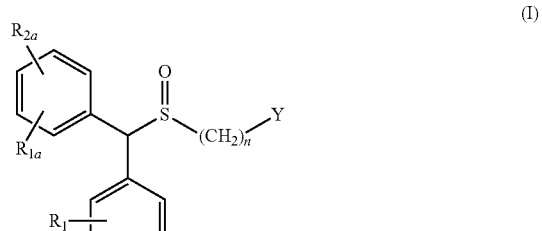

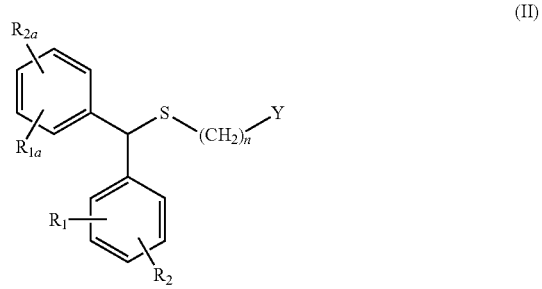

wherein n, Y, $R_1$, $R_{1a}$, $R_2$ and $R_{2a}$ are as defined in claim 1.

38 Claims, No Drawings

U.S. PATENT DOCUMENTS

| | | | |
|---|---|---|---|
| 2003/0220403 | A1 | 11/2003 | Corvari et al. |
| 2004/0048931 | A1 | 3/2004 | Heacock et al. |
| 2004/0102523 | A1 | 5/2004 | Broquaire et al. |
| 2004/0229940 | A1 | 11/2004 | Hassman et al. |
| 2004/0229941 | A1 | 11/2004 | Hassman et al. |
| 2004/0229942 | A1 | 11/2004 | Hassman et al. |
| 2004/0229943 | A1 | 11/2004 | Hughes et al. |
| 2004/0242698 | A1 | 12/2004 | Hughes |
| 2007/0021510 | A1 | 1/2007 | Hickey et al. |
| 2007/0293702 | A1 | 12/2007 | Braude et al. |
| 2009/0018202 | A1 | 1/2009 | Hickey et al. |
| 2009/0105346 | A1 | 4/2009 | Jegorov |
| 2009/0123545 | A1 | 5/2009 | Ron et al. |
| 2009/0156855 | A1 | 6/2009 | Barreca et al. |

FOREIGN PATENT DOCUMENTS

| | | |
|---|---|---|
| EP | 0 720 595 B1 | 12/1998 |
| EP | 1 260 501 A1 | 11/2002 |
| EP | 0 3292312 | 9/2003 |
| EP | 1 477 476 A1 | 11/2004 |
| GB | 1197809 | 7/1970 |
| WO | 99/25329 | 5/1999 |
| WO | 00/54648 | 9/2000 |
| WO | 01/12170 A2 | 2/2001 |
| WO | 01/13906 A2 | 3/2001 |
| WO | 01/22961 A1 | 4/2001 |
| WO | 02/10125 A1 | 2/2002 |
| WO | 2004/006905 A1 | 1/2004 |
| WO | 2004/060858 A1 | 7/2004 |
| WO | 2004/063149 A1 | 7/2004 |
| WO | 2004/101503 A1 | 11/2004 |
| WO | 2007/098273 A2 | 8/2007 |
| WO | 2008/149141 A2 | 12/2008 |
| WO | 2009/024863 A2 | 2/2009 |
| WO | 2009/025791 A2 | 2/2009 |
| WO | 2009/045488 A2 | 4/2009 |
| WO | 2009/090663 A1 | 7/2009 |

OTHER PUBLICATIONS

Babu et al., 1989, CAS: 111:114983.
Berge, S.M., et al., "Pharmaceutical Salts," *J. of Pharm. Sci.*, 1977, 66(1), 1-19.
Burgess, K., et al., "A facile route to homochiral sulfoxides," *Tetrahedron Letts.*, 1989, 30(28), 3633-3636.
Cotton, H., et al., "Asymmetric synthesis of esomeprazole," *Tetrahedron: Asymmetry*, 2000, 11(18), 3819-3825.
Faber, K., *Biotransformations in Organic Chemistry*, 3$^{rd}$ Ed., Springer (Ed.), 1997, 103-106 and 220-224.
Fernández, I., et al., "Recent developments in the synthesis and utilization of chiral sulfoxides," *Chem. Review*, 2002, A-BC.
Holland, H.L., et al., "An investigation of biotransformation of organic selenides by fungi," *Bioorg. Chem.*, 1983, 12, 1-7.
Holland, H.L., et al., "The oxidation of organic sulphides by *Mortierella isabellina*. 2. Effects of substituents on the stereochemistry of sulphoxide formation," *Can. J. Chem.*, 1985, 63, 1118-1120.
Kagan, H.B., et al., "Catalytic asymmetric synthesis; Asymmetric oxidation of sulfides" *VCH*, 1993, Ojima, I. (Ed.), 1993, 203-226.
Kagan, H.B., Synthesis of chiral sulfoxides by asymmetric oxidation, *Phosphorus and Sulphur*, 1986, 27, 127-132.
Madesclaire, M., "Synthesis of sulfoxides by oxidation of thioethers," *Tetrahedron*, 1986, 42(20), 5459-5495.
Ohta, H., et al., "Microbial asymmetric oxidation of 2-alkoxyethylsufides and a facile synthesis of chiral vinyl sulfoxide," *Chem. Lett.*, 1989, 625-628.
Ohta, H., et al., "Microbial oxidation of alkyl aryl sulfides to the corresponding optically active sulfoxides," *Agrig. Biol. Chem.*, 1985, 49, 671-676.
Pitchen, P., et al., "An efficient asymmetri oxidation of sulfides to sulfoxides," *J. Am. Chem. Soc.*, 1984, 106, 8188-8193.
Procter, D.J., "The synthesis of thiols, selenols, sulfides, selenides, sulfoxides, selenoxides, sulfones and selenones," *J. of Chem. Soc. Perkin Trans*, 1998, 641-667.
Rajendran et al., 2001, CAS: 135:204429.
Secundo, F., et al., "Asymmetric oxidation of sulfides by cyclohexanone monooxygenase," *Tetrahedron: Asymmetry*, 1993, 4(9), 1981-1982.
The European Search Report dated Feb. 11, 2004 (EP 03 292312).
Zhao, S.H., et al., "Asymmetric oxidation of sulfides mediated by chiral titanium complexes: mechanistic and synthetic aspects," *Tetrahedron*, 1987, 43(21), 5135-5144.
Zhao, S.H., et al., "Enantioselective oxidation of a sulfide: (S)-(–)-methyl *p*-tolyl sulfoxide," *Organic Syntheses, John Wiley & Sons Inc.*, 1993, VIII, 464-467.
Amiard, G., "No. 81.-Sur le dédoublement direct de la thréonine, par entrainement," *Bull. Soc. Chim. Fr.*, 1956, 447 (no English abstract).
Armodafinil Search, "Preliminary results from registry number search," Apr. 10, 2006, 1-36 and 1-296.
Bernstein, J., "Polymorphism in molecular crystals," *University Press, UK*, 2002, Chapter 10, 297-307.
Coquerel, G., "Review on the heterogeneous equilibria between condensed phases in binary systems of enantiomers," *Enantiomers, Gordon & Breach Science Publishers*, 2000, 5, 481-498.
Collet, A., et al., "Optical resolution by direct crystallization of enantiomer mixtures," *Chem. Rev.*, 1980, 80(3), 215-230.
Courvoisier, L., et al., "Influence of the process on the mechanisms and the performances of the preferential crystallization: example with (±)-5-4(4-Bromophenyl)-5-methylhydantoin," *Chemistry Letters*, 2001, 364-365.
De Min., M., et al., "Chiral resolutions, asymmetric synthesis and amplification of enantiomeric excess," *J. Chem. Phys.*, 1988, 85, 603-619.
Donovan, J.L., et al., "Chiral analysis of *d*- and *l*-modafinil in human serum: application to human pharmacokinetic studies," *Ther. Drug Monitoring*, 2003, 25, 197-202.
In, Y., et al., "Crystal and molecular structure of an (S)-(+)-enantiomer of modafinil, a novel wake-promoting agent," *Chem. Pharm. Bull.*, 2004, 52(10), 1186-1189.
Kim, S., et al., "A simple and mild esterification method for carboxylic acids using mixed carboxylic-carbonic anhydrides," *J. Org. Chem.*, 1985, 560-565.
Ndzié, E., et al., "An efficient access to the enantiomers of α-methyl-4-carboxyphenylglycine via a hydantoin route using a practical variant of preferential crystallization AS3PC (auto seeded programmed polythermic preferential crystallization)," *Tetrahedron Asymmetry*, 1997, 8(17), 2913-2920.
Prisinzano, T., et al., "Synthesis and determination of the absolute configuration of the enantiomers of modafinil," *Tetrahedron: Asymmetry*, 2004, 15, 1053-058.
Raynal, H., et al., "Disposition of modafinil enantiomers in humans and dogs," *ISSX Proceedings, Fifth European ISSX Meeting*, Tours, France, Sep. 26-29, 1993, 1 page.
Package Insert: FDA Approved Draft Labeling Text for NDA 20-717/ S-005 & S-008, PROVIGIL® (modafinil) Tablets [C-IV], Dec. 1998.
Kumar, "Approved and Investigational Uses of Modafinil", *Drugs*, 2008, 68(13), pp. 1803-1839.
Bastuji, H., et al., "Successful treatment of idiopathic hypersomnia and narcolepsy with modafinil, "*Prog. Neuropsych. Biol. Psych.*, 1988, 12, 695-700.
Drabowics, J., et al., "A convenient procedure for the oxidation of sterically hindered sulfides to sulfoxides," *Synthesis*, 1990, 937-938.
Duteil, J., et al., "Central α$_1$-adrenergic stimuation in relation to the behaviour stimulating effect of modafinil; studies with experimental animals," *Eur. J. Pharmacol.*, 1990, 180, 49-58.
Examiner's Search for U.S. Appl. No. 10/635,445; Jan. 2005.
Haleblian, J.K., "Characterization of Habits and Crystalline Modification of Solids and Their Pharmaceutical Applications," *J. of Pharm. Sciences*, 1975, 64(8), 1269-1288.
Bogan, R., et al., Armodafinil for excessive sleepiness associate with jet lag disorder. *Sleep*, 2009, 32(suppl):A52. Abstract 0153, Poster 256.

\* cited by examiner

PROCESS FOR ENANTIOSELECTIVE SYNTHESIS OF SINGLE ENANTIOMERS OF MODAFINIL BY ASYMMETRIC OXIDATION

CROSS-REFERENCE TO RELATED APPLICATIONS

This application is a continuation of U.S. application Ser. No. 12/050,666, filed Mar. 18, 2008, which is a continuation of U.S. application Ser. No. 11/082,530, filed Mar. 17, 2005 (U.S. Pat. No. 7,368,591, issued May 6, 2008), which is a continuation-in-part of U.S. application Ser. No. 10/943,360, filed Sep. 17, 2004 (U.S. Pat. No. 7,317,126, issued Jan. 8, 2008), which in turn claims priority of European Application No. EP 03292312.0, filed Sep. 19, 2003 and U.S. Provisional Application Ser. No. 60/507,089, filed Oct. 10, 2003. The disclosures of these priority applications are incorporated herein by reference in their entireties for all purposes.

FIELD OF THE INVENTION

The present invention relates to a process for enantioselective synthesis of the single enantiomers or an enantiomerically enriched form of modafinil and other structurally related compounds.

BACKGROUND OF THE INVENTION

Modafinil ($C_{15}H_{15}NO_2S$) of formula (A), also known as 2-(benzhydrylsulphinyl) acetamide or 2-[(diphenylmethyl) sulphinyl]acetamide, is a synthetic acetamide derivative with wake promoting activity, the structure and synthesis of which has been described in U.S. Pat. No. 4,177,290.

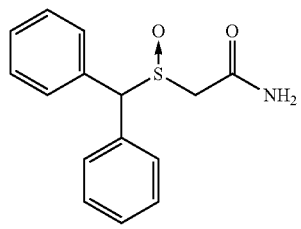

(A)

Modafinil has a stereogenic center at the sulphur atom and thus exists as two optical isomers, i.e. enantiomers.

Modafinil in its racemic form has been approved by the United States Food and Drug Administration for use in the treatment of excessive daytime sleepiness associated with narcolepsy.

U.S. Pat. No. 4,927,855 is related to modafinil enantiomers and particularly to the levorotary isomer and its use to treat depression and disorders present in patients suffering from Alzheimer disease.

According to this document, these enantiomers of modafinil are obtained by a process involving a chiral resolution method, which implies salt formation of the racemate of modafinic acid, also called benzhydrylsulphinyl acetic acid, with (−)-α-methylbenzylamine, a chiral, optically pure amine. The diastereoisomers obtained are then separated and finally one of the separated diastereoisomers is converted into the optically pure modafinic acid in a hydrolytic, or bond cleavage. The levorotary isomer of modafinic acid is thus obtained with very poor yields of about 21% from racemic modafinic acid.

Subsequently, the isolated enantiomer of modafinic acid has to be further processed by esterification and amidation steps, before the single enantiomer of modafinil can be obtained.

Thus, the modafinil enantiomer is obtained with a yield of about 6% from racemic modafinic acid, calculated on the basis of the yield of each step.

Considering alternative ways of obtaining enantiomerically pure modafinil, various metal-catalyzed enantioselective oxidations or stoichiometric transition-metal-promoted asymmetric reactions were described in the literature to prepare chiral sulphoxides by chemical oxidation of the corresponding sulphides (Kagan H. B. In "Catalytic Asymmetric Synthesis"; Ojima I., Ed. VCH: New York 1993, 203-226; Madesclaire M., Tetrahedron 1986; 42, 5459-5495; Procter D. J., Chem. Soc. PerkinTrans 1999; 835-872; Fernandez I. et al., Chem. Review 2002; A-BC). Metal-catalyzed enantioselective oxidations involve a metal catalyst complexed with a chiral ligand such as diethyl tartrate, $C_2$-symmetric diols or $C_3$-symmetric chiral trialkanolamine titanium(IV) complexes, $C_3$-symmetric trialkanolamine zirconium(IV) complex, chiral (salen) manganese(III) complex, chiral (salen) vanadium(IV) complex in the presence of various oxidants such as $H_2O_2$ tert-butyl hydroperoxide, cumene hydroperoxide. Methods based on chiral oxaziridines have also been used in the chemical oxidation of sulphides.

Some enzymatic methods for the asymmetric synthesis of fine chemicals were described in Kaber K. in "Biotransformations in Organic Chemistry", Springer Ed. 3$^{rd}$ ed. 1997 and reviewed by Fernandez I. et al. (Chem. Review 2002, A-BC). As an example, thioethers can be asymmetrically oxidized both by bacteria [e.g. *Corynebacterium equi* (Ohta H. et al. Agrig. Biol. Chem. 1985; 49:2229), *Rhodococcus equi* (Ohta H. et al. Chem. Lett. 1989; 625)] and fungi [*Helminthosporium* sp., *Mortieralla isabeffina* sp. (Holland H L. et al. Bioorg. Chem. 1983; 12:1)]. A large variety of aryl alkyl thioethers were oxidized to yield sulphoxides with good to excellent optical purity [(Ohta H. et al. Agrig. Biol. Chem. 1985; 49:671; Abushanab E. et al., Tetrahedron Lett. 1978; 19:3415; Holland H L. et al. Can. J. Chem. 1985; 63:1118)]. Mono-oxigenases and peroxidases are important class of enzymes able to catalyse the oxidation of a variety of sulphides into sulphoxides (Colonna S. et al. Tetrahedron: Asymmetry 1993; 4:1981). The stereochemical outcome of the enzymatic reactions has been shown to be highly dependant on the sulphide structure.

As an other alternative of the enzymatic approach, optically pure methyl arylsulphinylacetates with high enantiomeric excess (>98%) obtained by lipase-catalyzed resolution of the corresponding racemate were also described (Burgess K. et al. Tetrahedron Letter 1989; 30: 3633).

As an enantioselective oxidation method, an asymmetric sulphide oxidation process has been developed by Kagan and co-workers (Pitchen, P; Deshmukh, M., Dunach, E.; Kagan, H. B.; J. Am. Chem. Soc., 1984; 106, 8188-8193). In this process for asymmetric oxidation of sulphides to sulphoxides, the oxidation is performed by using tert-butyl hydroperoxide (TBHP) as oxidizing agent in the presence of one equivalent of a chiral complex obtained from $Ti(OiPr)_4/(+)$ or (−) diethyl tartrate/water in the molar ratio 1:2:1.

The general procedure for sulphide oxidation according to Kagan comprises first preforming the chiral complex at room temperature in methylene chloride before adding the sulphide. Then, the oxidation reaction is effected at −20° C. in the presence of tert-butyl hydroperoxide.

The direct oxidation of a variety of sulphides, notably for arylalkyl sulphides into optically active sulphoxides, with an enantiomeric excess (ee), in the range of 80-90%, can be achieved by this method.

More specifically, Kagan and co-workers reported that sulphoxide products could be obtained with high enantioselectivity when sulphides bearing two substituents of very different size were subjected to an asymmetric oxidation. For instance, when aryl methyl sulphides were subjected to oxidation, it was possible to obtain the aryl methyl sulphoxides in an enantiomeric excess (ee) of more than 90%.

Notably, cyclopropylphenyl sulphoxide is formed with 95% ee by this method.

However, asymmetric oxidation of functionalized sulphides, notably those bearing an ester function, was found to proceed with moderate enantioselectivity under these conditions.

Thus, compounds bearing on the stereogenic center, i.e. the sulphur atom, an alkyl moiety with an ester function close to the sulphur atom, such as methylphenylthioacetate, ethylmethylthioacetate and methylmethylthiopropanoate, are reported with ee of only 63-64% (H. B. Kagan, Phosphorus and Sulphur, 1986; 27, 127-132).

Similarly, oxidation of the aryl methyl sulphides with a methyl ester function in the ortho position of the aryl group yields low enantiomeric excess (60%) and yield (50%) as compared to the para substituted compound (ee 91%, yield 50%) or to the p-tolyl methyl sulphide (ee 91%, yield 90%) (Pitchen, P et al., J. Am. Chem. Soc., 1984; 106, 8188-8193).

Hence, even when the substituents on the sulphur atom differ in size, the presence of an ester function close to the sulphur atom strongly affects the enantioselectivity of the asymmetric oxidation.

These results also show that the enantioselectivity of this process highly depends on the structure and notably on the functionality of the substrate. More specifically, oxidation of sulphides bearing an ester function close to the sulphur gives little asymmetric induction.

Similarly, none of the enantioselective reactions so far reported in the literature deals with substrates bearing an acetamide or acetic acid moiety directly linked to the sulphur atom.

There have been attempts to improve the enantioselectivity by modifying some conditions for asymmetric oxidation of sulphides. For example, Kagan and co-workers (Zhao, S.; Samuel O.; Kagan, H. B., Tetrahedron 1987; 43, (21), 5135-5144) found that the enantioselectivity of oxidation could be enhanced by using cumene hydroperoxide instead of tert-butyl hydroperoxide (ee up to 96%). However, these conditions do not solve the problem of oxidation of sulphides bearing ester, amide or carboxylic acid functions close to the sulphur atom.

Thus, the applicant obtained crude (−)-modafinil with a typical enantiomeric excess of at most about 42% with the above method using the conditions described by Kagan H. B. (Organic Syntheses, John Wiley and Sons INC. ed. 1993, vol. VIII, 464-467) (refer to Example 17, comparative Example 1 below).

H. Cotton and co-workers (Tetrahedron: Asymmetry 2000; 11, 3819-3825) recently reported a synthesis of the (S)-enantiomer of omeprazole via asymmetric oxidation of the corresponding prochiral sulphide. Omeprazole, also called 5-methoxy-2-[[(4-methoxy-3,5-dimethyl-2pyridinyl)methyl]-sulphinyl]-1H-benzimidazole is represented by the following formula:

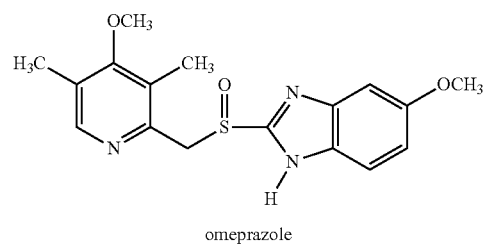

omeprazole

The asymmetric oxidation was achieved by titanium-mediated oxidation with cumene hydroperoxide (CHP) in the presence of (S,S)-(−) diethyl tartrate [(S,S)-(−)-DET]. The titanium complex was prepared in the presence of the prochiral sulphide and/or during a prolonged time and by performing the oxidation in the presence of N,N-diisopropylethylamine. An enantioselectivity of >94% was obtained by this method, whereas the Kagan's original method gives a modest enantiomeric excess of the crude product (30%).

According to the authors, the improved enantioselectivity of this process applied to omeprazole only is probably linked to the presence of benzimidazole or imidazole group adjacent to sulphur, which steers the stereochemistry of formed sulphoxide. The authors also suggested using this kind of functionality as directing groups when synthesizing chiral sulphoxides in asymmetric synthesis.

Hence, this publication is essentially focused on omeprazole, a pro-chiral sulphide bearing substituents of approximately the same size, and including an imidazole group which is described to play an important role in the asymmetric induction.

Therefore, there is a need for an improved enantioselective process for the manufacture of optically pure modafinil as well as other structurally related sulphoxides, notably 2-(benzhydrylsulphinyl)acetic acid and 2-(benzhydrylsulphinyl) alkyl acetate which overcomes the drawbacks of the prior art and, in particular, allows high yields.

SUMMARY OF THE INVENTION

The present invention provides a novel process for enantioselective synthesis of the single enantiomers of modafinil as well as other structurally related sulphoxides, in which process a surprisingly high enantioselectivity along with a high yield is obtained.

The novel process is characterized in that a pro-chiral sulphide is oxidized asymmetrically into a single enantiomer or an enantiomerically enriched form of the corresponding sulphoxide.

The invention also provides a process for preparing a sulphoxide as a single enantiomer or an enantiomerically enriched form from the corresponding pro-chiral sulphide with high purity, advantageously with a purity greater than 99.5%-99.8%.

The expression "pro-chiral sulphide(s)", as used herein, is understood to designate sulphides which after oxidation present a stereogenic center on the sulphur atom. Sulphides having further stereogenic centers elsewhere are thus also herein referred to as "pro-chiral sulphides".

This novel asymmetric oxidation process allows access to the compounds of interest with an extremely high enantiomeric excess, even if the corresponding pro-chiral sulphides are functionalized, i.e. have ester, amide, carboxylic acid or nitrile substituents.

The process is simple with a one step reaction making the process suitable for large scale production of enantiomeric compounds in a high yield and high enantiomeric excess.

As a further advantage, this process implements low amounts of a titanium compound as a catalyst which is environmentally non-toxic and relatively low-cost.

Advantageously, modafinil can be obtained as a single enantiomer or in an enantiomerically enriched form, more directly, without having to go through a chiral resolution method of modafinic acid.

The invention also provides several processes for preparing modafinil as a single enantiomer or in an enantiomerically enriched form. Advantageously, these processes are limited to three steps or even less when using benzhydrol or benzhydrylthiol as starting material and modafinil single enantiomer is obtained with high yields.

DETAILED DESCRIPTION OF ILLUSTRATIVE EMBODIMENTS

It has been found that the asymmetric oxidation of modafinil precursors, in particular diphenylmethylthioacetic acid, the amide and the esters thereof could be achieved with surprisingly high enantioselectivity up to 99.5% by effecting the titanium chiral complex mediated reaction in the presence of a base.

The invention relates to a method for preparing a sulphoxide compound of formula (I) either as a single enantiomer or in an enantiomerically enriched form:

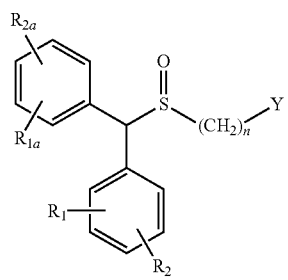

(I)

wherein:

Y is —CN, —C(=O)X wherein X is selected from, —NR$_3$R$_4$, —OH, —OR$_5$, —NHNH$_2$;

R$_1$, R$_{1a}$, R$_2$ and R$_{2a}$ are the same or different and are selected from H, halo, (C$_1$-C$_8$)alkyl, (C$_2$-C$_8$)alkenyl, (C$_2$-C$_8$)alkynyl, (C$_6$-C$_{10}$)aryl, (C$_5$-C$_{10}$)heteroaryl, —CN, —CF$_3$, —NO$_2$, —OH, (C$_1$-C$_8$)alkoxy, —O(CH$_2$)$_m$NR$_6$R$_7$, —OC(=O)R$_8$, —OC(=O)NR$_6$R$_7$, —C(=O)OR$_8$, —C(=O)R$_8$, —O(CH$_2$)$_m$OR$_8$, —(CH$_2$)$_m$OR$_8$, —NR$_6$R$_7$, —C(=O)NR$_6$R$_7$;

R$_3$ and R$_4$ are the same or different and are each selected from H, (C$_1$-C$_6$) alkyl, hydroxy(C$_1$-C$_8$)alkyl, —NHOH or OH, or R$_3$ and R$_4$ may also be taken together with the N atom through which R$_3$ and R$_4$ are linked to form a 5 to 7 membered N-heterocyclic group;

R$_5$ represents alkyl, cycloalkyl, aralkyl, alkaryl, or aryl;

R$_6$ and R$_7$ are the same or different and selected from H, (C$_1$-C$_6$)alkyl, hydroxy(C$_1$-C$_6$)alkyl, or R$_6$ and R$_7$ may also be taken together with the N atom through which R$_6$ and R$_7$ are linked to form a 5 to 7 membered N-heterocyclic group;

R$_8$ represents H, alkyl, cycloalkyl, aralkyl, alkaryl, or aryl;

n is 1, 2 or 3; and m is from 1, 2, 3, or 4;

comprising the steps of:

a) contacting a pro-chiral sulphide of formula (II)

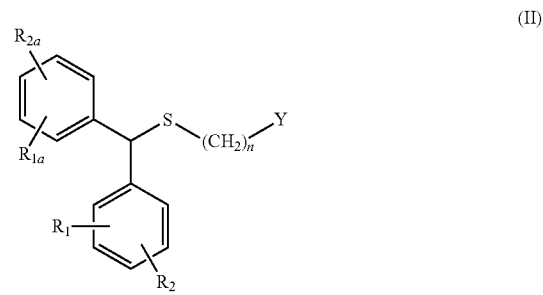

(II)

wherein R$_1$, R$_2$, R$_{1a}$, R$_{2a}$, Y and n are as defined above, with a metal chiral ligand complex, a base and an oxidizing agent in an organic solvent; and optionally b) isolating the obtained sulphoxide of formula (I).

The method allows to prepare sulphoxides of formula (I) with an enantiomeric excess of generally more than about 80%. Advantageously, preferred enantiomeric excess is of more than 80%, preferably of more than 90%, more preferably of more than 95%, and most preferably of 99% and more.

The method allows also to prepare sulphoxides of formula (I) with a degree of purity higher than 90%, preferably of more than 98%, more preferably superior to 99%.

For a pair of enantiomers, enantiomeric excess (ee) of enantiomer E1 in relation to enantiomer E2 can be calculated using the following equation:

$$\% \text{ enantiomeric excess} = \frac{(E1 - E2)}{(E1 + E2)} \times 100$$

The relative amount of E1 and E2 can be determined by chiral HPLC (High Performance Liquid Chromatography).

The purity refers to the amount of the enantiomers E1 and E2, relative to the amount of other materials, which may notably, include by-products such as sulphone, and the unreacted sulphide. The purity may be determined by HPLC as well.

As used herein, the term "about" refers to a range of values ±10% of the specified value. For example, "about 20" includes ±10% of 20, or from 18 to 22.

As used herein, the term "a metal chiral ligand complex" refers to a complex composed of a metal compound, a chiral ligand and, optionally, water.

The term "chiral ligand" is a group which includes at least one chiral center and has an absolute configuration. A chiral ligand has a (+) or (−) rotation of plane polarized light.

In the above definition, "alkyl" means an aliphatic hydrocarbon group which may be straight or branched having 1 to 12 carbon atoms in the chain. Preferred alkyl groups have 1 to 6 carbon atoms in the chain.

"Lower alkyl" means about 1 to about 4 carbon atoms in the chain which may be straight or branched. "Branched" means that one or more alkyl groups, such as methyl, ethyl or propyl, are attached to a linear alkyl chain. The alkyl may be substituted with one or more "cycloalkyl group". Exemplary alkyl groups include methyl, ethyl, n-propyl, i-propyl, n-butyl, i-butyl, t-butyl, n-pentyl, cyclopentylmethyl.

"Cycloalkyl" means a non-aromatic mono- or multicyclic ring system of 3 to 10 carbon atoms, preferably of about 5 to about 10 carbon atoms. Exemplary monocyclic cycloalkyl groups include cyclopentyl, cyclohexyl, cycloheptyl and the like.

"Aralkyl" means an aryl-alkyl group wherein the aryl and alkyl are as herein described. Preferred aralkyls contain a lower alkyl moiety. Exemplary aralkyl groups include benzyl, 2-phenethyl and naphthalenemethyl.

"Aryl" means an aromatic monocyclic or multicyclic ring system of 6 to 10 carbon atoms. The aryl is optionally substituted with one or more "ring system substituents" which may be the same or different, and are as defined herein. Exemplary aryl groups include phenyl or naphthyl.

"Alkaryl" means an alkyl-aryl group, wherein the aryl and alkyl are as defined herein. Exemplary alkaryl groups include tolyl.

"Halo" means an halogen atom and includes fluoro, chloro, bromo, or iodo. Preferred are fluoro, chloro or bromo, and more preferred are fluoro or chloro.

"Alkenyl" means an aliphatic hydrocarbon group containing a carbon-carbon double bond and which may be straight or branched having 2 to 8 carbon atoms in the chain. Preferred alkenyl groups have 2 to 4 carbon atoms in the chain. Branched means that one or more lower alkyl groups such as methyl, ethyl or propyl are attached to a linear alkenyl chain. The alkenyl group may be substituted by one or more halo or cycloalkyl group. Exemplary alkenyl groups include ethenyl, propenyl, n-butenyl, i-butenyl, 3-methylbut-2-enyl, n-pentenyl, heptenyl, octenyl, cyclohexyl-butenyl and decenyl.

"Alkynyl" means an aliphatic hydrocarbon group containing a carbon-carbon triple bond and which may be straight or branched having 2 to 8 carbon atoms in the chain. Preferred alkynyl groups have 2 to 4 carbon atoms in the chain. "Branched" means that one or more lower alkyl groups such as methyl, ethyl or propyl are attached to a linear alkynyl chain. The alkynyl group may be substituted by one or more halo. Exemplary alkynyl groups include ethynyl, propynyl, n-butynyl, 2-butynyl, 3-methylbutynyl, n-pentynyl, heptynyl, octynyl and decynyl.

"Alkoxy" means an alkyl-O— group wherein the alkyl group is as herein described. Preferred alkoxy groups have 1 to 6 carbon atoms in the chain, and more preferably 2 to 4 carbon atoms in the chain. Exemplary alkoxy groups include methoxy, ethoxy, n-propoxy, i-propoxy, n-butoxy and heptoxy.

"Heteroaryl" means an aromatic monocyclic or multicyclic ring system of 5 to 10 carbon atoms, in which one or more of the carbon atoms in the ring system is/are hetero element(s) other than carbon, for example nitrogen, oxygen or sulfur. Preferred ring sizes of rings of the ring system include about 5 to about 6 ring atoms. The "heteroaryl" may also be substituted by one or more "ring system substituents" which may be the same or different, and are as defined herein. A nitrogen atom of an heteroaryl may be a basic nitrogen atom and may also be optionally oxidized to the corresponding N-oxide. Exemplary heteroaryl and substituted heteroaryl groups include pyrazinyl, thienyl, isothiazolyl, oxazolyl, pyrazolyl, furazanyl, pyrrolyl, 1,2,4-thiadiazolyl, pyridazinyl, quinoxalinyl, phthalazinyl, imidazo[1,2-a]pyridine, imidazo[2,1-b] thiazolyl, benzofurazanyl, azaindolyl, benzimidazolyl, benzothienyl, thienopyridyl, thienopyrimidyl, pyrrolopyridyl, imidazopyridyl, benzoazaindole, 1,2,4-triazinyl, benzthiazolyl, furanyl, imidazolyl, indolyl, indolizinyl, isoxazolyl, isoquinolinyl, isothiazolyl, oxadiazolyl, pyrazinyl, pyridazinyl, pyrazolyl, pyridyl, pyrimidinyl, pyrrolyl, quinazolinyl, quinolinyl, 1,3,4-thiadiazolyl, thiazolyl, thienyl and triazolyl. Preferred heteroaryl groups include pyrazinyl, thienyl, pyridyl, pyrimidinyl, isoxazolyl and isothiazolyl.

"Hydroxyalkyl" means a HO-alkyl-group wherein alkyl is as herein defined. Preferred hydroxyalkyls contain lower alkyl. Exemplary hydroxyalkyl groups include hydroxymethyl and 2-hydroxyethyl.

"N-heterocyclic group" means a non-aromatic saturated monocyclic system of 5 to 7 ring members comprising one nitrogen atom and which can contain a second heteroelement such as nitrogen, oxygen and sulphur. The heterocyclyl may be optionally substituted by one or more "ring system substituents" which may be the same or different, and are as defined herein. When a second heteroelement selected from a nitrogen or a sulphur atom is present, this heteroelement of the N-heterocyclic group may also be optionally oxidized to the corresponding N-oxide, S-oxide or S,S-dioxide. Preferred N-heterocyclic group includes piperidyl, pyrrolidinyl, piperazinyl, morpholinyl, and the like. The N-heterocyclic group is optionally substituted with one or more "ring system substituent". Preferred N-heterocyclic group substituents include $(C_1-C_4)$alkyl, $(C_6-C_{10})$aryl, optionally substituted with one or more halogen atoms, such as the substituent parachlorophenyl.

"Ring system substituents" mean substituents attached to aromatic or non-aromatic ring systems inclusive of H, halo, $(C_1-C_8)$alkyl, $(C_2-C_8)$alkenyl, $(C_2-C_8)$alkynyl, $(C_6-C_{10})$aryl, $(C_5-C_{10})$heteroaryl, —CN, —CF$_3$, —NO$_2$, —OH, $(C_1-C_8)$ alkoxy, —O(CH$_2$)$_m$NRR', —OC(=O)R, —OC(=O)NRR', —O(CH$_2$)$_m$OR, —CH$_2$OR, —NRR', —C(=O)NRR', —C(=O)OR and —C(=O)R, wherein R and R' are H, alkyl, cycloalkyl, aralkyl, alkaryl or aryl or for where the substituent is —NRR', then R and R' may also be taken together with the N-atom through which R and R' are linked to form a 5 to 7 membered N-heterocyclic group.

In the case of X=OH, the sulphoxide of formula (I) may be obtained as a salt, notably as an alkaline salt, such as a sodium, potassium, lithium salt or ammonium salt or pharmaceutically acceptable salts.

"Pharmaceutically acceptable salts" means the relatively non-toxic, inorganic and organic acid addition salts, and base addition salts, of compounds of the present invention. These salts can be prepared in situ during the final isolation and purification of the compounds. In particular, acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, tosylate, citrate, maleate, fumarate, succinate, tartrate, naphthylate, mesylate, glucoheptonate, lactiobionate, sulphamates, malonates, salicylates, propionates, methylene-bis-b-hydroxynaphthoates, gentisates, isethionates, di-p-toluoyltartrates, methane-sulphonates, ethanesulphonates, benzene-sulphonates, p-toluenesulphonates, cyclohexylsulphamates and quinateslauryl-sulphonate salts, and the like (see, for example, S. M. Berge, et al., <<Pharmaceutical Salts>>, J. Pharm. Sci., 66: p. 1-19 (1977) which is incorporated herein by reference. Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, lithium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide. Suitable amine base addition salts are prepared from amines which have sufficient basicity to form a stable salt, and preferably include those amines which are frequently used in medicinal chemistry because of their low toxicity and acceptability for medical use. Exemplary base addition salts include the ammonia, ethylenediamine, N-methyl-glucamine, lysine, arginine, ornithine, choline, N,N'-dibenzylethylenediamine, chloroprocaine, diethanolamine, procaine, N-benzyl-phenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like.

As used herein, "between [ . . . ]-[ . . . ]" refers to an inclusive range.

According to a preferred aspect, $R_1$, $R_2$, $R_{1a}$ and $R_{2a}$ are independently selected from the group consisting of H and halo, halo being preferably F.

Preferably, one of $R_1$, $R_2$ and/or $R_{1a}$, $R_{2a}$ is H and the other one is F. The fluorine atom may be located on the ortho, meta, para position, the para position being preferred.

Preferably, n is 1.

Most preferably, the sulphoxides prepared by the novel process are sulphoxides of formula (I) in which Y is CN or Y is —C(═O)X.

Preferably, X is —NR$_3$R$_4$, —OH, —OR$_5$, more preferably —NR$_3$R$_4$ and most preferably —NH$_2$ or —NHOH.

Preferably, R$_5$ is alkyl or aralkyl. Preferred R$_5$ group includes notably methyl, ethyl, i-propyl, benzyl and tolyl.

Most preferably, the sulphoxide prepared by the novel method is modafinil, which corresponds to the sulphoxide of formula (I), wherein n is 1, $R_1$, $R_2$, $R_{1a}$ and $R_{2a}$ are H and Y is —C(═O)X with X═NH$_2$.

As used herein, "modafinic acid", also called "diphenylmethylsulphinylacetic acid", refers to the compound of formula (I), wherein n is 1, $R_1$, $R_2$, $R_{1a}$ and $R_{2a}$ are H and X is OH.

As used herein, an "ester of modafinic acid" refers to a compound of formula (I), wherein n is 1, $R_1$, $R_2$, $R_{1a}$ and $R_{2a}$ are H and X is —OR$_5$.

Step a)

The oxidation reaction is carried out in an organic solvent. Surprisingly, the solvent is not as essential for the enantioselectivity of the oxidation, according to the invention. The solvent may hence be chosen with respect to suitable conditions from an industrial point of view, as well as environmental aspects. Suitable organic solvents are notably toluene, ethyl acetate, tetrahydrofuran, acetonitrile, acetone and methylene chloride and can be readily determined by one skilled in the art. From an environmental point of view, non-chlorinated solvents are preferred. In this regard, ethyl acetate and toluene are particularly preferred.

Preparation of the Metal Chiral Ligand Complex

The metal chiral ligand complex is prepared from a chiral ligand and a metal compound.

The metal compound is preferably a titanium, a zirconium, a vanadium or a manganese compound and more preferably a titanium compound.

Thus, preferred metal chiral ligand complexes are notably titanium, zirconium, vanadium or manganese chiral ligand complexes, more preferably a titanium chiral ligand complex.

The titanium compound is generally a titanium (IV) compound, preferably a titanium (IV) alkoxide, such as, in particular, titanium (IV) isopropoxide or propoxide.

The chiral ligand is a chiral compound capable of reacting with the titanium compound. Such compounds are preferably chosen from hydroxy substituted compounds, preferably having more than one hydroxy group. Thus, the chiral ligand is preferably a chiral alcohol, such as a $C_2$-symmetric chiral diol or a $C_3$-symmetric chiral triol. The chiral alcohol may be branched or unbranched alkyl alcohol, or an aromatic alcohol.

Preferred chiral ligands are binaphtol, mandelic acid, hydrobenzoin, esters of tartaric acid, such as (+)-dialkyl-L-tartrate or (−)-dialkyl-D-tartrate, preferably (+)-di($C_1$-$C_4$) alkyl-L-tartrate or (−)-di($C_1$-$C_4$)alkyl-D-tartrate, notably (+)-dimethyl-L-tartrate or (−)-dimethyl-D-tartrate, (+)-diethyl-L-tartrate or (−)-diethyl-D-tartrate, (+)-diisopropyl-L-tartrate or (−)-diisopropyl-D-tartrate, (+)-dibutyl-L-tartrate or (−)-dibutyl-D-tartrate and (+)-ditertbutyl-L-tartrate or (−)-ditertbutyl-D-tartrate. Especially preferred are (+)-diethyl-L-tartrate and (−)-diethyl-D-tartrate.

Preferred chiral ligands also include $C_3$-symmetric trialkanolamines, notably of formula (1):

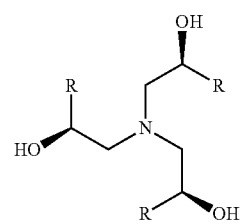

(1)

wherein R is a lower alkyl or aryl, as for example methyl, t-butyl and phenyl. Preferred chiral ligands also include Schiff base of general formula (2a) or (2b):

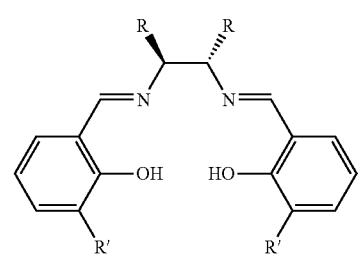

(2a)

wherein R is the same and represents a lower alkyl or aryl, such as methyl or phenyl, or are attached together to form a cycloalkyl group such as cyclohexyl; R' is a lower alkyl or alkoxy;

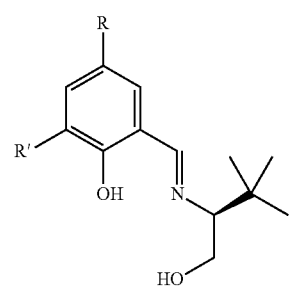

(2b)

wherein R is a lower alkyl or NO$_2$;
R' is a lower alkyl or alkoxy.

These Schiff bases may form a chiral ligand complex with the metal, known as chiral (salen)-metal complex.

Preferred examples of metal chiral ligand complexes are $C_2$-symmetric diols or $C_3$-symmetric trialkanolamine titanium (IV) complexes, $C_3$-symmetric trialkanolamine zirconium (IV) complexes, chiral (salen) manganese (III) complexes, chiral (salen) vanadium (IV) complexes, notably those disclosed in Fernandez et al., American Chemical Society, 2002, A-BC.

Especially preferred metal chiral ligand complexes are titanium chiral diol complexes and most preferably diethyl tartrate titanium (IV) complexes.

The stoichiometry of the metal chiral ligand complex may vary and is not critical for the invention.

In particular, the ratio of the chiral ligand with respect to the metal compound may vary from 1 to 4 equivalents and is preferably 2 equivalents.

In accordance with a preferred aspect of the invention, the preparation of the metal chiral complex further comprises water. Indeed, it has been found that the presence of water in the metal chiral ligand complex further improves the enantioselectivity of the reaction.

The amount of water involved in the metal chiral ligand complex may vary from 0.1 to 1 equivalent with respect to the titanium compound. In an especially preferred embodiment, the amount of water ranges from 0.4 to 0.8 equivalent with respect to the metal compound.

Thus it is not necessary to pre-dry the reactants. According to another particular embodiment, no water is added, the water present in the reaction mixture being provided only by the residual humidity of the reactants.

The amount of the metal chiral ligand complex used in the process is not critical. It has however been found advantageous to use less than 0.50 equivalent with respect to the pro-chiral sulphide, especially 0.05-0.30 equivalent, and most preferably 0.1-0.30 equivalent. Surprisingly, even very low amounts of complex, such as for instance 0.05 equivalent may be used in the process according to the invention with excellent results.

The metal chiral ligand complex may be prepared in the presence of the pro-chiral sulphide or before the pro-chiral sulphide is added to the reaction vessel.

According to one preferred embodiment, the preparation of the metal chiral ligand complex is performed in the presence of the pro-chiral sulphide, i.e. the pro-chiral sulphide is loaded into the reaction vessel before the components used for the preparation of the chiral complex are introduced.

The reaction time of the metal chiral ligand complex depends on the temperature.

Indeed, it has been found that the reaction kinetics of the metal chiral ligand complex appear to depend on the couple temperature and reaction time. Thus, the higher the temperature, the lower the reaction time is. Inversely, the lower the temperature, the longer the reaction time is.

As an example, at an elevated temperature, which as used herein means a temperature between 20-70° C., preferably of about 40-60° C., most preferably of about 50-55° C., less than two hours are generally sufficient to form the metal chiral ligand complex. As an example, at 55° C., the metal chiral ligand complex may be formed in about 50 minutes. At a lower temperature, such as at 25° C., the metal chiral ligand complex may be formed in about 24 hours.

Introduction of a Base

The asymmetric oxidation according to the invention is carried out in the presence of a base.

Indeed, the enantioselectivity of the reaction is surprisingly enhanced when a base is present during oxidation. Enantioselectivities of more than 99% may be thus observed. The order of introduction of the base is not critical, provided that it is added before the oxidizing agent. The base may be introduced before or after the pro-chiral sulphide and, preferably after the metal chiral ligand complex is formed.

Preferably, the base is introduced after the metal chiral ligand complex is formed, and after the pro-chiral sulphide is added.

In another preferred embodiment, the base is contacted with the metal chiral ligand complex and the pro-chiral sulphide for few minutes, preferably for at least 3 minutes before adding the oxidant in order to increase the enantioselectivity.

According to a preferred embodiment of the invention, the base is introduced at the temperature at which the oxidation reaction is carried out, hereafter called "oxidation temperature".

The base should be soluble in the reaction mixture. Preferably, it is an organic base, such as for instance an amine. Especially suitable bases are amines, preferably tertiary amines, such as triethylamine, N,N-diisopropylethylamine, dimethyl-ethanolamine, triethanolamine and, most preferably, N,N-diisopropyl-ethylamine and triethylamine.

The amount of base added to the reaction mixture should not exceed a certain value, because it may affect the enantioselectivity of the reaction. In particular, an amount of less than 2 equivalents, notably of 0.5 equivalent with respect to pro-chiral sulphide, especially of 0.01 to 2 equivalents, preferably of 0.05 to 0.5 equivalent and most preferably of 0.1 to 0.3 equivalent, has proven to be advantageous.

Oxidation

Surprisingly, the process does not require very low temperatures such as −20° C., as described by Kagan and co-workers as essential to obtain a good enantioselectivity. This feature is particularly interesting since such low temperatures result in long reaction times.

The temperature will however be chosen such as to avoid decomposition of the reactants and excessive reaction times.

In a preferred embodiment, the oxidizing agent is contacted with the sulphide, the metal chiral ligand complex and the base at a temperature between 0-60° C., preferably 15-40° C. and more preferably at room temperature, that is between about 20-25° C.

A suitable oxidizing agent for the asymmetric oxidation may be a hydroperoxide, preferably hydrogene peroxide, tert-butylhydroperoxide or cumene hydroperoxide, and most preferably the latter.

The oxidizing agent is left in contact with the other reactants during a sufficient period to achieve satisfactory conversion rate, but not too long in order not to affect the purity and the enantioselectivity of the product obtained.

In a preferred embodiment, the oxidizing agent is left in contact with the other reactants during about 30 minutes to 3 hours.

The amount of the oxidizing agent is not critical with respect to the enantioselectivity of the reaction. However, an excessive amount of oxidizing agent may affect the purity of the product obtained by favouring the formation of sulphone.

An amount of oxidizing agent of less than 2 equivalents relative to the amount of sulphide amide is generally preferred and an especially preferred amount is 0.8 to 1.2 equivalents and more preferably 1.0 equivalent.

Step b)

The sulphoxide formed during the oxidation reaction may be isolated according to conventional procedures.

Thus, as described in the literature, the reaction mixture may be treated with water or an aqueous sodium hydroxide solution, which results in the formation of a gel containing metal salts. This gel may be filtered off and thoroughly washed with an organic solvent. The filtrate may be extracted with an organic solvent. It may also be crystallized in an organic or aqueous solvent to obtain the desired enantiomer.

According to an advantageous aspect of the invention, the obtained sulphoxide forms a precipitate that can be directly isolated by filtration and optionally washed with water or an organic solvent such as ethyl acetate, toluene, ethanol, methylene chloride. Advantageously, the precipitate is a crystalline and highly pure form. Thus, advantageously, the method avoids cumbersome subsequent treatments mentioned above.

Step c)

In accordance with a preferred embodiment, the method further comprises a step c) of crystallization of the isolated product obtained in step b).

Such crystallization step may be useful to improve the purity of the isolated product and/or to produce a desired polymorphic form and/or to improve the enantiomeric excess of the targeted enantiomer and/or to obtain lots with a specific particle size.

In this regard, it can be made reference to WO 2004/060858 in which polymorphic forms of modafinil enantiomers were disclosed. As an example, (−)-modafinil obtained under form II may be converted into form I by a crystallization step c), Forms I and II being as defined in WO 2004/060858.

The crystallization may be carried out in organic solvents optionally in admixture with water. Suitable organic solvent are notably alcohols, ketones, esters, ethers, chlorinated solvents, polar and aprotic solvents and mixtures thereof, or mixture with water.

Examples of alcohols include methanol, ethanol, propanol, isopropyl alcohol, tert-butanol, 2 methyl-1-butanol, benzyl alcohol.

Among the chlorinated solvents, dichloromethane may be mentioned.

Among the ketones, acetone, methylethylketone, 2 pentanone, cyclohexanone may be mentioned.

Among the ethers, tetrahydrofuran, dioxane, may be mentioned.

Other suitable solvents can be readily determined by one skilled in the art.

Surprisingly, it has been found that the presence of water in the crystallization solvent allows to reach an enhanced enantiomeric excess and purity. In addition, a crystallization step using an organic solvent/water mixture produce a polymorphic form I and advantageously allows to reduce the volume of organic solvent utilized in the process.

Thus, preferred crystallization solvents are alcoholic solvents, and mixtures of organic solvents with water, more preferred are mixtures of organic solvents with water, most preferred are organic solvent mixed with up to 40% water. Are particularly preferred mixtures of organic solvents with up to 25% of water.

The product obtained in step b) if needed may also further be enantiomerically enriched. Such methods are known in the art and include notably preferential crystallization.

Thus in a particular embodiment of the invention, the method further comprises a step of preferential crystallization for improving the enantiomeric excess.

Such a method of optical resolution by preferential crystallization of (±) modafinic acid has been disclosed in the French patent application WO 2004/060858.

The obtained enantiomer may further be processed to produce lots with a specific particle size. Conventional methods as milling, sieving, micronization, comminution, separation by weight or by density are known by those skilled in the art. An appropriate method for the preparation of lots of modafinil having bounded defined particle diameter range is notably disclosed in WO 2004/006905.

The enantiomers of the sulphoxide compounds of formula (1), wherein Y is —C(=O)X and X is —OH or X is —OR$_5$, may be converted into their corresponding amide, that is a sulphoxide compound of formula (I) wherein X=—NH$_2$.

The enantiomers of modafinic acid or the ester thereof obtained by the above method may further be converted into the corresponding amide, that is modafinil enantiomers.

Thus, in accordance with a particular embodiment, esters of modafinic acid enantiomers may be converted into the corresponding modafinil enantiomers by an amidation reaction, notably with ammonia.

Hence, modafinic acid may be converted into modafinil by:
   esterification of the carboxylic acid function by any suitable method such as, for example, by reaction with a lower alkyl alcohol, in presence of dimethylsulfate. The obtained corresponding ester may then be transformed by
   amidation of the resulting ester by any suitable method, notably in presence of ammonia.

Such methods have been disclosed notably in U.S. Pat. No. 4,927,855.

In accordance with another particular embodiment, the enantiomers of the sulphoxide compounds of formula (I) wherein Y is CN may be converted into their corresponding amide, that is a sulphoxide compound of formula (I) wherein Y is C(=O)X, X being NH$_2$.

This conversion may be realized by any suitable method known in the art. Examples of such suitable methods are notably oxidation or hydrolysis of the nitrile group, for instance, by catalytic phase transfer with peroxides or by basic or acid hydrolysis with an appropriate inorganic base or acid in mild experimental conditions.

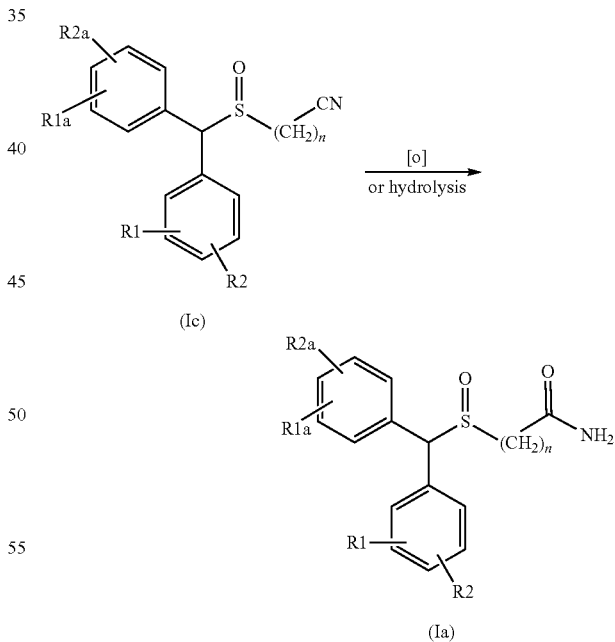

Thus, the desired enantiomer of modafinil may be prepared from diphenylmethylsulphinylacetonitrile enantiomers, for example by oxidation with hydrogen peroxide in the presence of tetrabutylammonium hydrogen sulfate in alkaline conditions or also by direct basic or acidic hydrolysis.

In accordance with another embodiment, the method according to the invention implements a sulphide of formula (II), wherein Y=C(=O)X, X being NHOH, which may be prepared according to any suitable method known in the art and notably to the method disclosed in U.S. Pat. No. 4,098,824.

In accordance with another embodiment, the method according to the invention implements a sulphide of formula (IIa) wherein Y is C(=O)X and X is $NH_2$.

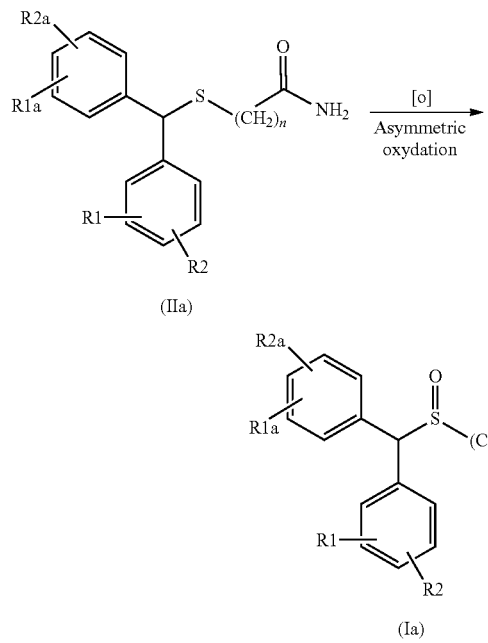

Preparation of Sulphides of Formula (II)

Sulphides of formula (II) may be prepared by any suitable method known in the art.

By way of example, sulphides of formula (IIa) may be prepared from the corresponding sulphide of formula (IIb) wherein Y is C(=O)X and X is $OR_5$.

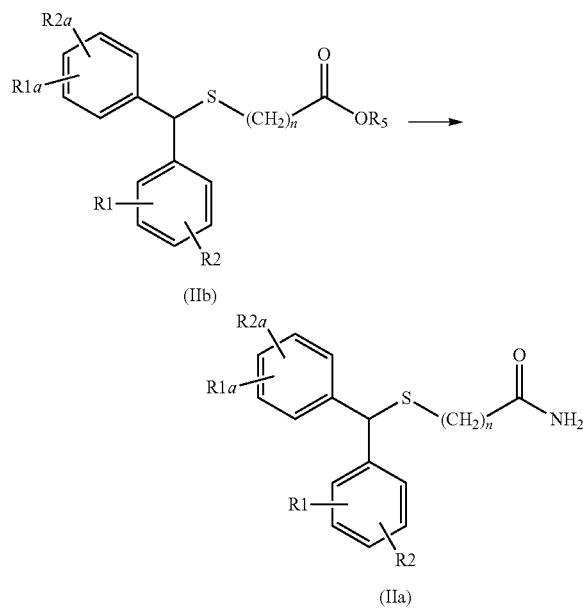

The sulphide of formula (IIb) may be prepared from an appropriately substituted benzhydrol:

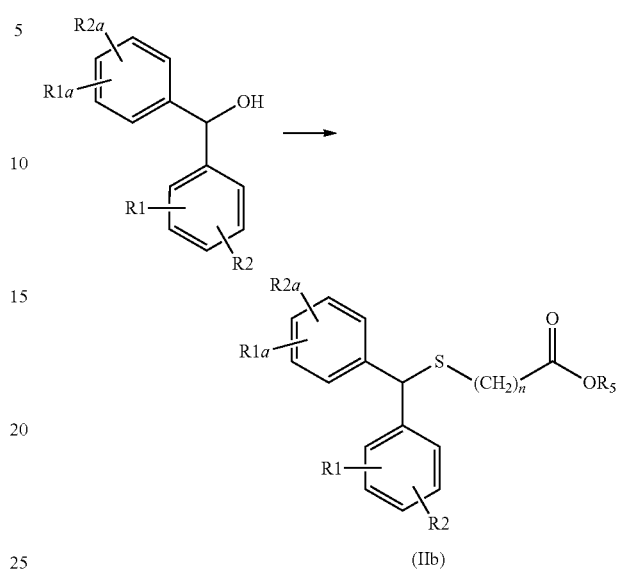

In accordance with a preferred embodiment, the sulphide of formula (IIa) is the sulphide wherein $R_1$, $R_{1a}$, $R_2$, $R_{2a}$ are H, n is 1, so called diphenylmethylthio-acetamide, which may be prepared from sulphide ester of formula (IIb), in which $R_5$ is alkyl, preferably ($C_1$-$C_4$)alkyl, notably methyl, so called methyldiphenylmethylthio-acetate (MDMTA).

Such sulphide ester of formula (IIb) and notably MDMTA may be prepared from benzhydrol.

In a preferred embodiment, MDMTA is prepared according to the method comprising the steps of:
 a1) conversion of benzhydrol into benzhydryl carboxylate, notably into the benzyhydryl acetate, and
 b1) conversion of benzhydryl carboxylate, notably the benzhydryl acetate into MDMTA.

These steps a1) and b1) may be effected by any appropriate method, preferably steps a1) and b1) are performed according to the method disclosed in WO 2004/063149.

As an example, modafinil enantiomers may be prepared according to the following reaction steps:

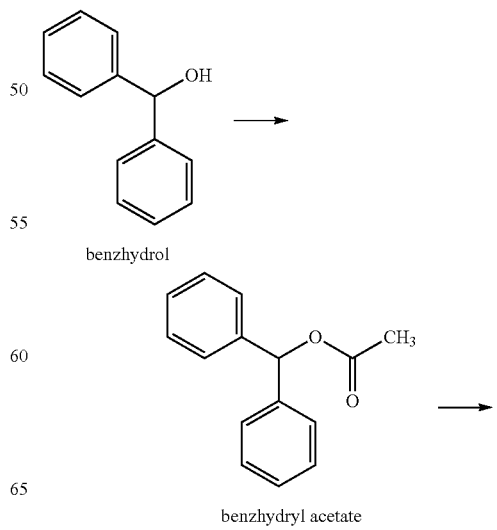

benzhydrol benzhydryl acetate

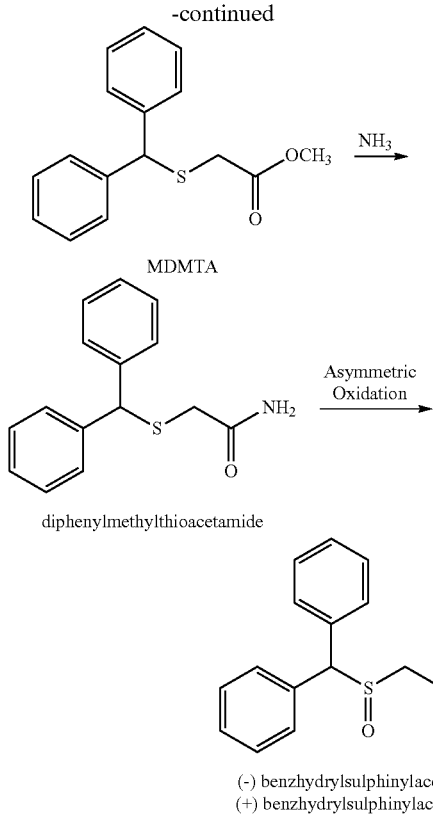

MDMTA diphenylmethylthioacetamide (-) benzhydrylsulphinylacetamide
(+) benzhydrylsulphinylacetamide Other routes for preparing diphenylmethylthioacetamide may be used.

By way of example, diphenylmethylthioacetamide, also called benzhydryl-thioacetamide, may be prepared from benzhydrol according to a process comprising:

(1) reacting benzhydrol with a suitable acid and thiourea to form a S-benzhydrylthiouronium salt;
(2) reacting the S-benzhydrylthiouronium salt with a suitable base to form benzhydrylthiol;
(3) reacting the benzhydrylthiol with chloroacetamide to form 2-(benzhydrylthio)acetamide.

This process is illustrated by scheme 1.

Scheme 1

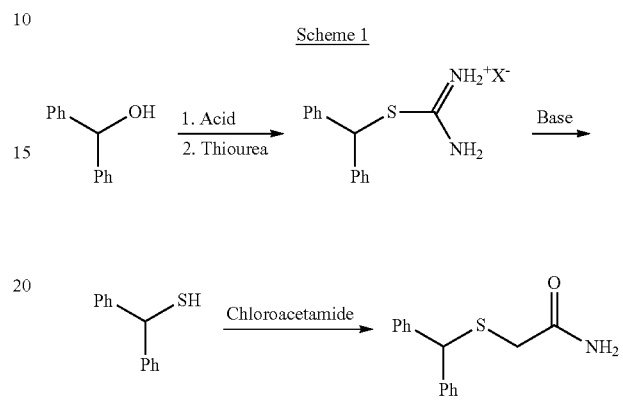

In the alternative, diphenylmethylthioacetamide may be prepared by the process comprising the steps of:

(1) converting the hydroxyl group of benzhydrol into a leaving group;
(2) converting the obtained product
    directly into diphenylmethylthioacetamide, or,
    into alkyl diphenylmethylthioacetate and then into diphenylmethylthio-acetamide.

This method is illustrated by scheme 2:

Scheme 2

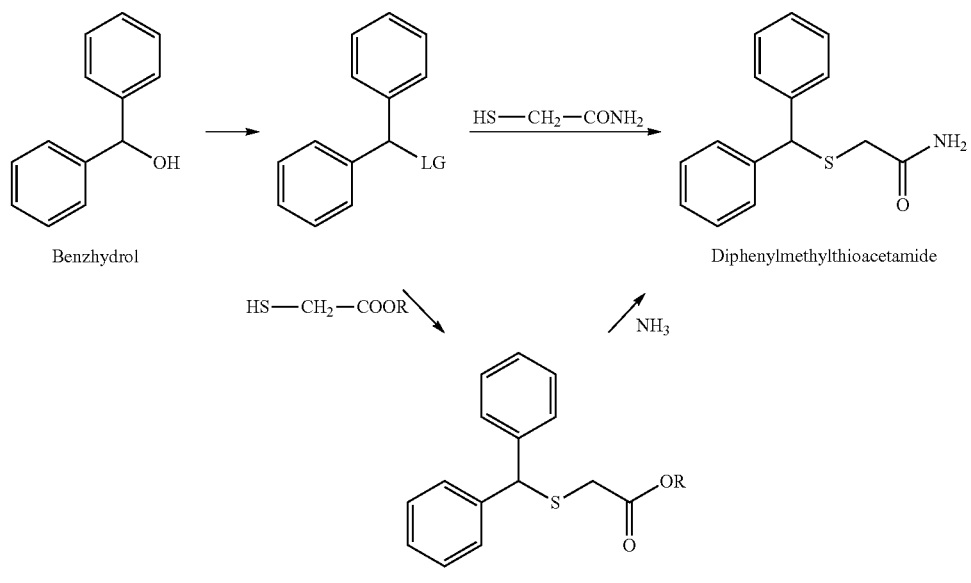

R = alkyl

"LG" = leaving group

Under the terms "leaving group" is understood any group that can be removed easily by a nucleophilic reactant. Leaving groups may be selected from the group consisting of halogens, such as chloro- and bromo-radicals, or sulphonyl groups, such as methanesulphonyl- or p-toluenesulphonyl- radicals, or acetate radicals.

The first step of this process may be realized by any methods known from the person skilled in the art.

As an example, the hydroxyl group of benzhydrol may be converted into chloro- or bromo-radical by reacting benzhydrol with thionyl chloride or thionyl bromide.

As an example, the hydroxyl group of benzhydrol may be converted into methanesulphonate group or into p-toluenesulphonate group by reacting benzhydrol respectively with methanesulphonyl chloride or p-toluenesulphonyl chloride.

As an example, the hydroxyl group of benzhydrol may be converted into an acetate radical by reacting benzhydrol with acetyl chloride or acetic anhydride.

As a further alternative, diphenylmethylthioacetamide may be prepared by a process comprising the steps of:
  reacting benzhydrol with alkylthioglycolate in the presence of a Lewis acid and,
  reacting the alkyldiphenylmethylthioacetate obtained with ammonia, as illustrated by scheme 3.

Scheme 3

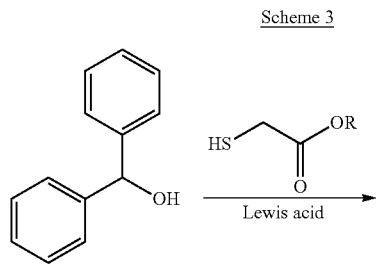

Benzhydrol

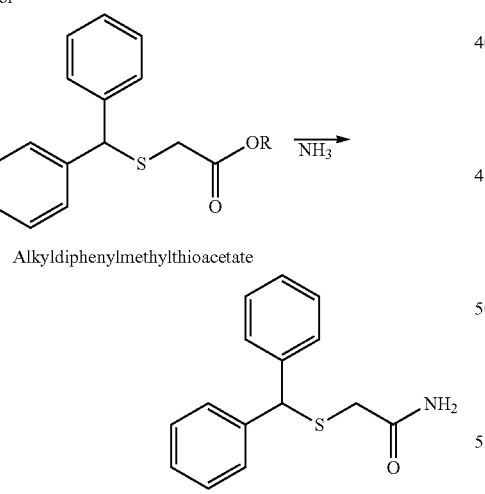

Alkyldiphenylmethylthioacetate

Preferably, the Lewis acid is chosen from $ZnCl_2$, $ZnBr_2$, $ZnI_2$.

Diphenylmethylthioacetamide may also be prepared from benzhydrylthiol.

In that case, diphenylmethylthioacetamide is prepared by a process comprising the steps of:
  (1) reacting benzhydrylthiol with alkylchloroacetate, and,
  (2) reacting the obtained alkyldiphenylmethylthioacetate with ammonia.

The process is illustrated by scheme 4:

Scheme 4

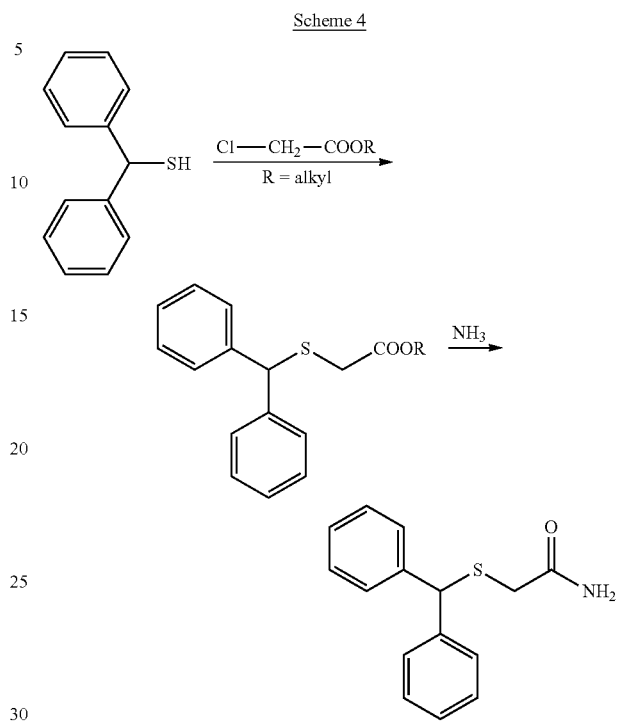

Another possibility is to prepare diphenylmethylthioacetamide by a process comprising the steps of:
  (1) reacting benzhydrylthiol with chloroacetonitrile, and
  (2) oxidizing or hydrolyzing the obtained diphenylmethylthioacetonitrile into diphenylmethylthioacetamide.

This process is illustrated by scheme 5.

Scheme 5

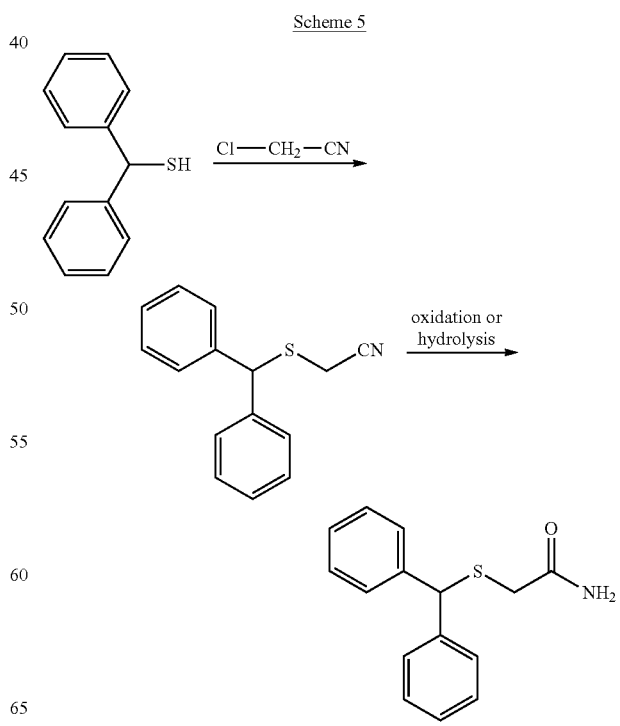

According to another process, diphenylmethylthioacetamide may be prepared by the process comprising the steps of:

(1) reacting benzhydrylthiol with a base, such as potassium hydroxide;
(2) reacting the obtained product with a methylene halide;
(3) reacting the obtained product with a cyanide salt;
(4) oxidizing or hydrolyzing the obtained diphenylmethylthioacetonitrile into diphenylmethylthioacetamide.

This route is illustrated by scheme 6:

Scheme 6

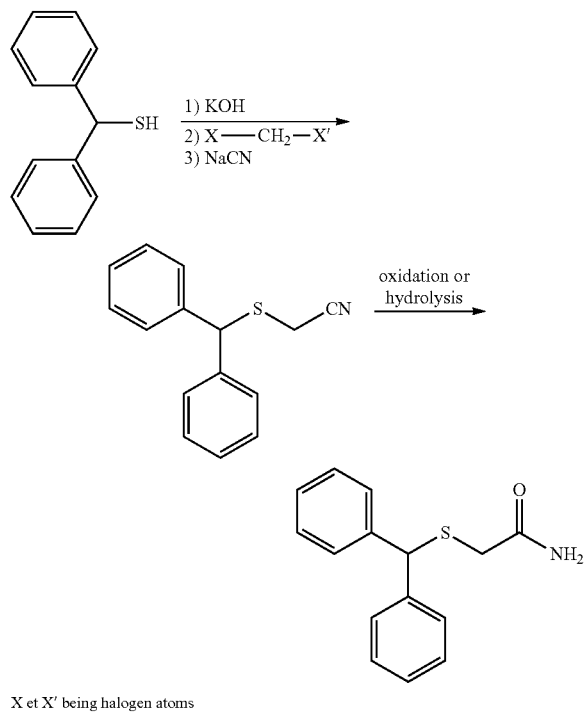

X et X' being halogen atoms

Finally, diphenylmethylthioacetamide may be prepared from diphenylmethyl-thioacetic acid by the process comprising:

(1) reacting diphenylmethylthioacetic acid with an halogenating agent such as thionyl chloride or a carboxylic acid activating agent, and
(2) reacting the obtained product with NH₃.

This route is illustrated by scheme 7.

Scheme 7

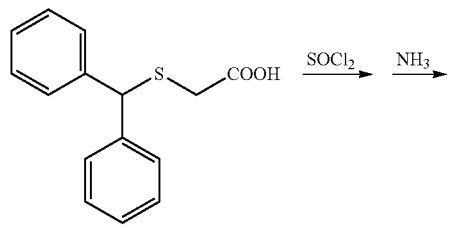

Diphenylmethylthioacetic acid

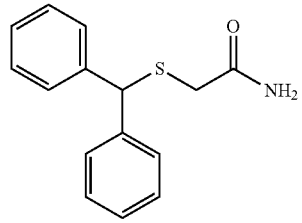

Finally, diphenylmethylthioacetic acid may be prepared according to the route of scheme 1 to 6 notably.

The invention is illustrated more in detail by the following examples.

EXAMPLES

Material and Methods

Determination of the Enantiomeric Excess in the Examples and Comparative Examples The enantiomeric excess value in each example given above gives an indication of the relative amounts of each enantiomer obtained. The value is defined as the difference between the relative percentages for the two enantiomers.

The enantiomeric composition of the obtained sulphoxide has been determined by chiral High Performance Liquid Chromatography (HPLC under the following conditions:
  Column: AGP (150×4.0 mm; 5 µm)
  Oven temperature: 40° C.
  Eluent: sodium acetate+0.5% n-butanol
  Flow: 0.9 ml/min
  Wavelength: DAD λ=230 nm
  As an example:
  Retention time for the (−)-2-[(diphenyl)methylsulphinyl]acetamide: 6.5 min.
  Retention time for the (+)-2-[(diphenyl)methylsulphinyl]acetamide: 8.3 min.
or,
  Column: chiralpak AS (250×4.6 mm)
  Oven temperature: 40° C.
  Eluent: isopropanol/ethanol 85/15
  Flow: 0.45 ml/min
  Wavelength: 222 nm
  As an example:
  Retention time for the (−)-2-[(diphenyl)methylsulphinyl]acetamide: 27.2 min.
  Retention time for the (+)-2-[(diphenyl)methylsulphinyl]acetamide: 14.6 min.
or,
  Column: chiralpak AS (250×4.6 mm)
  Oven temperature: 30° C.
  Eluent: ethanol
  Flow: 0.5 ml/min
  Wavelength: 220 nm
  As an example:
  Retention time for the methyl(−)-2-[(diphenyl)methylsulphinyl]acetate: 11.4 min.
  Retention time for the methyl(+)-2-[(diphenyl)methylsulphinyl]acetate: 10.2 min.

Determination of the Purity in the Examples and Comparative Examples

The purity value in each example is defined as the ratio of the amount of enantiomers obtained after filtration with respect to the total amount of products present. Studied impurities measured were mainly the unchanged parent compound (pro-chiral sulphide) and the sulphone resulting from an over oxidation during the process, potential degradation products, intermediates of the synthesis of the pro-chiral sulphide.

The purity of the obtained sulphoxide has been determined by High Performance Liquid Chromatography (HPLC) under the following conditions:

Column: Zorbax RX C8 (150×4.6 mm; 5 µm) or Zorbax Eclipse XDB C8 (150×4.6 mm; 5 µm)

Oven temperature: 25° C.

Eluent:

A=water+0.1% trifluoroacetic acid

B=nitrile acetate+0.1% trifluoroacetic acid with a gradient of 90% A to 100% B in 20 minutes Flow: 1 ml/min Wavelength: DAD λ=230 nm (column Zorbax RX C8) 220 nm (column Zorbax Eclipse XDB C8)

As an example (column Zorbax RX C8):

Retention time for the 2-[(diphenyl)methylsulphinyl]acetamide: 8.8 min.

Retention time for the 2-[(diphenyl)methylthio]acetamide: 11.8 min.

Retention time for the 2-[(diphenyl)methylsulphonyl]acetamide: 10.5 min.

Examples 1 to 16

Asymmetric synthesis of (−)-2-(diphenylmethyl)sulphinylacetamide

General Procedure for Examples 1 to 16

Diphenylmethylthioacetamide (7.70 g; 0.03 mol; 1.0 eq) was dissolved in the solvent (77 mL; 10 vol.). To the solution were added (S,S)-(−)-diethyl-tartrate (1.23 g; 0.006 mol; 0.2 eq) and titanium (IV) tetraisopropoxide (0.85 g; 0.88 mL; 0.003 mol; 0.1 eq) and water (27 µL minus the sum of water present in reactants and solvent already introduced; 0.0015 mol; 0.05 eq) at 55° C. In these conditions, the resulting chiral titanium complex has the stoichiometry (DET/Ti(OiPr)$_4$/H$_2$O: 2/1/0.5) and corresponds to 0.1 eq with respect to diphenylmethylthioacetamide. Stirring was maintained at 55° C. during 50 minutes.

After cooling to room temperature (25° C.), were added to the mixture diisopropylethylamine (0.39 g; 0.52 mL; 0.003 mol; 0.1 eq) and cumene hydroperoxide (4.55 g; 5.0 mL; 0.03 mol; 1.0 eq).

After contacting during about an hour, the formed precipitate is isolated by filtration.

All the following experiments were performed in accordance with the conditions of the general procedure, by modifying parameters as indicated in tables 1-17.

Example 1

Influence of the Ratio of the Titanium Chiral Complex with Respect to the Diphenylmethylthioacetamide on the Enantioselectivity and the Purity of the Asymmetric Oxidation In this experiment, the ratio of the titanium chiral complex with respect to the diphenylmethylthioacetamide was varied from 0.05 to 0.3 equivalent, the stoichiometry of the chiral titanium complex DET/Ti(O-iPr)$_4$/water: 2/1/0.4 being maintained constant, all the others parameters being as defined in the above general procedure. Experiments were performed in toluene.

TABLE 1

| Entry | Titanium complex/ sulphide (equivalent) | Scale (mole) | E.e. (%) | Purity (%) | Yield (%) |
|---|---|---|---|---|---|
| 1 | 0.30/1 | 0.03 | >99.5 | >99.5 | 88.4 |
| 2 | 0.15/1 | 0.06 | 93.6 | >99 | 89.7 |
| 3 | 0.10/1 | 0.09 | 93 | >99 | 92 |
| 4 | 0.05/1 | 0.18 | 92 | 95.5 | 95.4 |

E.e. = enantiomeric excess

In experiments 1 to 4, the enantioselectivity was equal or superior to 92%, and increased up to more than 99.5 with the amount of titanium chiral ligand complex involved in the reaction mixture. The purity was superior to 99% except for the lowest ratio titanium chiral ligand complex/diphenylmethylthioacetamide. Yields were superior or equal to 88.4%.

Example 2

Influence of the Amount of Water on the Enantioselectivity and the Purity of the Asymmetric Oxidation In this experiment, the amount of water was varied with respect to the titanium tetraisopropoxide from 0 to 1 equivalent, all other parameters being as defined in the above general procedure. Notably, the ratio of the titanium chiral ligand complex was maintained at 0.1 equivalent with respect to the diphenylmethylthioacetamide. Experiments were performed in toluene.

TABLE 2

| Entry | Amount of water (equivalent) | E.e. (%) | Purity (%) | Yield (%) |
|---|---|---|---|---|
| 1 | 0 | 80 | — | 90.3 |
| 2 | 0.4 | 93 | >99 | 92 |
| 3 | 0.8 | 94 | >99 | 88 |
| 4 | 1 | 91 | 99.5 | 90 |

E.e. = enantiomeric excess;
— = Not determined

These results showed that the amount of water had an effect on the enantioselectivity of the reaction. Thus, the best enantioselectivities were achieved when an amount of water used comprised between 0.4 and 0.8 equivalent. On the opposite, the enantioselectivity drops notably in the absence of water. A purity superior or equal to 99% and high yields (88%-92%) were obtained.

Example 3

Influence of the Nature of the Solvent on the Enantioselectivity and the Purity of the Asymmetric Oxidation As reported in table 3, experiments were performed in various solvents, the conditions being the same as in the above general procedure.

TABLE 3

| Entry | Solvent | E.e. (%) | Purity (%) | Yield (%) |
|---|---|---|---|---|
| 1 | Toluene | 99.4 | 99.7 | 80 |
| 2 | Ethyl Acetate | 99.5 | 99.7 | 73.5 |
| 3 | Methylene Chloride | 98 | 98.8 | 61 |
| 4 | Acetonitrile | 99.3 | 98.8 | 70.2 |
| 5 | Tetrahydrofuran | 99.7 | 99.6 | 50.7 |
| 6 | Acetone | 99.6 | 99.2 | 45.8 |

E.e. = enantiomeric excess

In all experiments, the sulphoxide amide was obtained with a high enantioselectivity (E.e. equal or superior to 99%) as well as with a high purity (purity equal or superior to 98.8%), except when methylene chloride is used as solvent. In this experimental condition the enantioselectivity was slightly lower being, nevertheless, equal to 98%.

Example 4

Influence of the Nature of the Base on the Enantioselectivity and the Purity of the Asymmetric Oxidation The bases N,N-diisopropylethylamine and triethylamine were compared with regard to the enantioselectivity, the purity and the yield obtained either in toluene or in ethyl acetate as solvent. The other parameters were maintained as defined in the general procedure.

TABLE 4

| Entry | Base | Solvents | E.e. (%) | Purity (%) | Yield (%) |
|---|---|---|---|---|---|
| 1 | Diisopropylethylamine | toluene | 93 | >99 | 92 |
| 2 | Triethylamine | toluene | 94 | >99.5 | 90.3 |
| 3 | Diisopropylethylamine | ethylacetate | 99.5 | >99.5 | 73.5 |
| 4 | Triethylamine | ethylacetate | 99 | >99.5 | 79.2 |

E.e. = enantiomeric excess

High enantioselectivities and yields were obtained as reported in table 4.

In ethylacetate, higher enantioselectivities (>99%) and lower yields (73.5%-79.2%) were obtained with triethylamine and diisopropylethylamine. On the opposite, in the presence of diisopropylethylamine and triethylamine lower enantioselectivities (93-94%) but higher yields (around 90.3%-92%) were observed in toluene.

The purity level was similar in both solvents (superior to 99% or 99.5%) when the two bases were added to the reaction medium.

Example 5

Influence of the Amount of Base on the Enantioselectivity and the Purity of the Asymmetric Oxidation The ratio of base was varied from 0 to 0.2 equivalent with regard to diphenylmethylthioacetamide.

TABLE 5

| Entry | Base | Amount of base (eq) | Solvents | E.e. (%) | Purity (%) | Yield (%) |
|---|---|---|---|---|---|---|
| 1 | — | — | toluene | 66 | >99 | 86 |
| 2 | — | — | ethylacetate | 74 | >99 | 70 |

TABLE 5-continued

| Entry | Base | Amount of base (eq) | Solvents | E.e. (%) | Purity (%) | Yield (%) |
|---|---|---|---|---|---|---|
| 3 | Diisopropyl-ethylamine | 0.1 | toluene | 93 | >99 | 92 |
| 4 | Triethylamine | 0.1 | ethylacetate | 99 | >99.5 | 79.2 |
| 5 | Triethylamine | 0.2 | ethylacetate | 94.3 | >99.8 | 78.6 |

E.e. = enantiomeric excess

In the absence of base, the reaction rate was slow and the enantioselectivity was weak (66%-74% range).

The reaction rate increased with the addition of a base in the reaction mixture. The enantioselectivity was very high when 0.1 equivalent of triethylamine was added to the reaction mixture and ethylacetate used as solvent. It can be noticed that the enantioselectivity was slightly decreased when the amount of base used was increased up to 0.2 equivalent.

The amount of base has only a little effect on the purity which remained always superior to 99%.

In addition, the contact time between the catalyst and the base was a factor increasing the enantioselectivity. A contact time of at least 3 minutes between the catalyst and the base increased the enantiomeric excess by about 5%. As an example the enantiomeric excess increased from 94.1% (no contact time) to 99.5% (contact time of 3 minutes).

Example 6

Influence of the Temperature of Formation of the Titanium Chiral Ligand Complex on the Enantioselectivity and the Purity of the Asymmetric Oxidation The titanium chiral ligand complex DET/Ti/$H_2O$ (2/1/0.5) was prepared at a temperature selected in the 25° C. to 70° C. range according to the above described procedure, the solvent used in the experiments being ethyl acetate. The enantioselectivity and the purity obtained were compared.

TABLE 6

| Entry | Temperature (° C.) | E.e. (%) | Purity (%) | Yield (%) |
|---|---|---|---|---|
| 1 | 25 | 65.6 | >99 | 63.5 |
| 2 | 50 | >99.5 | 99.9 | 69.6 |
| 3 | 55 | 99 | >99.5 | 79.2 |
| 4 | 60 | >99.5 | 99.9 | 73 |
| 5 | 70 | 99.7 | 99.8 | 62 |

E.e. = enantiomeric excess

The preparation of the titanium chiral ligand complex at 25° C. during 50 minutes results in a lower enantioselectivity. At higher temperature 50° C.-70° C., a highly enriched enantiomeric (99%→99.5%) and highly pure (>99.5%-99.9%) form of the sulphoxide is obtained.

Example 7

Influence of the Time of Formation of the Chiral Ligand Titanium Complex on the Enantioselectivity and the Purity of the Asymmetric Oxidation The time of formation of the titanium chiral ligand complex was varied from 10 minutes to 50 minutes in ethyl acetate as solvent, the other parameters being as defined in the above general procedure.

TABLE 7

| Entry | Time (minutes) | E.e. (%) | Purity (%) | Yield (%) |
|---|---|---|---|---|
| 1 | 10 | 87.5 | >99.5 | 79.7 |
| 2 | 30 | 91 | 99.5 | 79.2 |
| 3 | 50 | 99 | >99.5 | 79.2 |

E.e. = enantiomeric excess

A time of formation of 50 minutes is necessary and sufficient to obtain an enantioselectivity close to superior to 99% as well as a purity superior or equal to 99.5%.

As reported in table 8 showing the results of experiments performed at 25° C., a prolonged reaction time of at least 24 hours was required to form the titanium chiral ligand complex and to achieve a better enantioselectivity.

TABLE 8

| Entry | Temperature (° C.) | Time | E.e. (%) | Purity (%) | Yield (%) |
|---|---|---|---|---|---|
| 1 | 25 | 50 min | 65.6 | >99 | 63.5 |
| 2 | 25 | 1 hr | 78.4 | 99.1 | 72.0 |
| 3 | 25 | 3 hrs | 86.4 | 99.4 | 74.6 |
| 4 | 25 | 8 hrs | 89.6 | 99.0 | 75.8 |
| 5 | 25 | 14 hrs | 92.2 | 99.5 | 74.6 |
| 6 | 25 | 24 hrs | 94.2 | 97.0 | 85.5 |

E.e. = enantiomeric excess

Example 8

Influence of the Temperature of the Oxidation Reaction on the Enantioselectivity and the Purity of the Asymmetric Oxidation The oxidation step, corresponding to the introduction of the oxidizing agent, was carried out at a temperature selected from 0° C. to 55° C. in ethyl acetate as solvent, the other parameters being as defined in the above general procedure.

TABLE 9

| Entry | Temperature | E.e. % | Purity % | Yield (%) |
|---|---|---|---|---|
| 1 | 0° C. | 99.7 | 99.7 | 52.6 |
| 2 | 10° C. | 99.5 | 99.7 | 65.0 |
| 3 | 20° C. | 99.5 | 99.8 | 73.9 |
| 4 | 25° C. | 99 | >99.5 | 79.2 |
| 5 | 55° C. | 94.3 | 97.8 | 81.8 |

E.e. = enantiomeric excess

All experimental conditions lead to high enantiomeric excesses and high purities, in the 94.3%-99.7% range and in the 97.8%-99.7% range, respectively.

At a temperature of 55° C., the enantiomeric excess was decreased slightly by about 5% from 99.5% to 94.3%. The sulphoxide was produced with a higher yield (81.8%) but with a slightly lower purity (97.8%).

Example 9

Influence of the Addition Time of the Oxidizing Agent on the Enantioselectivity and the Purity of the Asymmetric Oxidation The impact of addition time of the oxidizing agent on the enantioselectivity of the reaction was tested. Thus, cumene hydroperoxide (CuOOH) was added upon either 5 or 40 minutes (in this assay, the oxidant was diluted in ethylacetate), the other parameters being as defined in the above general procedure and the reaction performed in ethyl acetate.

TABLE 10

| Entry | Time (minutes) | E.e. (%) | Purity (%) | Yield (%) |
|---|---|---|---|---|
| 1 | 5 | 99 | >99.5 | 79.2 |
| 2 | 40* | >99.8 | 99.5 | 64.7 |

E.e. = enantiomeric excess;
*CuOOH was diluted in ethyl acetate.

The addition time of the oxidizing agent did not have a significant influence on the enantioselectivity or the purity.

Example 10

Influence of the Nature of the Chiral Ligand on the Enantioselectivity and the Purity of the Asymmetric Oxidation Table 11 reports chiral ligands and the solvents assayed, the other parameters being as defined in the above general procedure.

TABLE 11

| Entry | Chiral ligand | Solvent | E.e. (%) | Purity (%) | Yield (%) |
|---|---|---|---|---|---|
| 1 | (S,S)-(−)-DET | ethyl acetate | 99 | >99.5 | 79.2 |
| 2 | (S,S)-(−)-DET | toluene | >99.5 | >99.5 | 88.4 |
| 3 | (R,R)-(+)-DET | toluene | 98.6 | >99.5 | 98.5 |
| 4 | (S,S)-(−)-DIT | ethyl acetate | 92.5 | 99.2 | 73.9 |

E.e. = enantiomeric excess;
DET = diethyl tartrate;
DIT = Diisopropyl tartrate

In the experimental conditions selected, an enantioselectivity equal to 92.5% or in the 98→99.5% range and a purity in the 99.2→99.5% range were obtained when using diethyltartrate or diisopropyl tartrate as chiral ligands.

Example 11

Influence of the Order and of the Temperature of Introduction of Reagents on the Enantioselectivity and the Purity of the Asymmetric Oxidation The following experiments were performed in ethyl acetate. Quantities used were as defined in the general protocol above.

TABLE 12

| | Reagents introduction: order and temperature | | | | | | E.e. | Purity | Yield |
|---|---|---|---|---|---|---|---|---|---|
| Entry | 1/T | 2/T | 3/T | 4/T | 5/T | 6/T | % | % | % |
| 1 | DET/ 20° C. | SA/ 20° C. | Ti(OiPr)$_4$/ 50° C. | H$_2$O/ 50° C. | Et$_3$N/ 20° C. | CHP/ 20° C. | 99.4 | 99.7 | 67.2 |

TABLE 12-continued

| | Reagents introduction: order and temperature | | | | | E.e. | Purity | Yield |
|---|---|---|---|---|---|---|---|---|
| Entry | 1/T | 2/T | 3/T | 4/T | 5/T | 6/T | % | % | % |
| 2 | DET/ 20° C. | SA/ 20° C. | Et$_3$N/ 50° C. | Ti(OiPr)$_4$/ 50° C. | H$_2$O/ 50° C. | CHP/ 20° C. | 99.6 | 99.8 | 78.9 |
| 3 | DET/ 20° C. | SA/ 20° C. | Ti(OiPr)$_4$/ 50° C. | Et$_3$N/ 50° C. | H$_2$O/ 50° C. | CHP/ 20° C. | 99.6 | 99.7 | 77.6 |
| 4 | DET/ 20° C. | Ti(OiPr)$_4$/ 50° C. | H$_2$O/ 50° C. | SA/ 50° C. | Et$_3$N/ 20° C. | CHP/ 20° C. | 98.8 | 99.6 | 64.2 |
| 5 | DET/ 20° C. | Ti(OiPr)$_4$/ 50° C. | H$_2$O/ 50° C. | SA/ 20° C. | Et$_3$N/ 20° C. | CHP/ 20° C. | 99.0 | 99.6 | 69.0 |
| 6 | DET/ 20° C. | Ti(OiPr)$_4$/ 50° C. | H$_2$O/ 50° C. | Et$_3$N/ 20° C. | SA/ 20° C. | CHP/ 20° C. | 98.6 | 99.4 | 68.4 |
| 7 | DET/ 20° C. | Ti(OiPr)$_4$/ 50° C. | H$_2$O/ 50° C. | Et$_3$N/ 50° C. | SA/ 50° C. | CHP/ 20° C. | 98.8 | 99.7 | 77.5 |
| 8 | DET/ 20° C. | SA/ 20° C. | Ti(OiPr)$_4$/ 50° C. | H$_2$O/ 50° C. | Et$_3$N/ 50° C. | CHP/ 20° C. | 99.0 | 99.7 | 78.1 |

E.e. = enantiomeric excess; DET = (S,S)-(−)diethyl tartrate; Ti(OiPr)$_4$ = titaniumtetraisopropoxide; SA = sulphide amide; Et$_3$N = triethylamine; CHP = cumene hydroperoxide.

The reagents introduction order and temperature influenced only slightly the enantioselectivity (98.6-99.6% range) and the purity (99.4-99.8% range) of the asymmetric oxidation of the sulphide amide studied, provided that the triethylamine was added before the oxidant.

Example 12

Influence of the Contact Time of the Oxidant in the Reaction Mixture on the Enantioselectivity and the Purity of the Asymmetric Oxidation The experiment was performed according to the general procedure in ethyl acetate as solvent. The contact time between the oxidant and the reaction mixture was studied at room temperature.

TABLE 13

| Entry | Contact time | E.e. (%) | Purity (%) | Sulphone amide (%) | Sulphide amide (%) |
|---|---|---|---|---|---|
| 1 | 30 min | 99.6 | 99.66 | 0.04 | 0.28 |
| 2 | 1 hr | 99.6 | 99.77 | 0.05 | 0.17 |
| 3 | 2 hrs | 99.6 | 99.75 | 0.06 | 0.17 |
| 4 | 3 hrs | 98.8 | 99.78 | 0.06 | 0.15 |
| 5 | 4 hrs | 97.0 | 99.73 | 0.07 | 0.16 |
| 6 | 5 hrs | 96.4 | 99.83 | 0.07 | 0.09 |
| 7 | 6 hrs | 96.8 | 99.82 | 0.07 | 0.09 |
| 8 | 20.5 hrs | 95.5 | 99.77 | 0.10 | 0.12 |
| 9 | 24 hrs | 94.6 | 99.85 | 0.08 | 0.07 |
| 10 | 48 hrs | 94.2 | 99.85 | 0.09 | 0.06 |

E.e. = enantiomeric excess

The global yield of the reaction was 76.8%. The contact time between the oxidant and other reagents weakly influence the enantioselectivity of the reaction which is slightly decreased with time although remaining acceptable (> to 94%).

The purity remains high (increasing from 99.66% to 99.85%) with time. The levels of sulphone amide increased slightly from 0.04% to 0.1% over a 48 hour period while the sulphide amide decreased from 0.28% to 0.1% with time. The best ratios of enantioselectivity over purity were obtained within 3 hours post the oxidant introduction in the reaction mixture.

Example 13

Influence of the Quantity of Oxidant on the Enantioselectivity and the Purity of the Asymmetric Oxidation In the general experimental procedure defined above, the quantity of oxidant was varied between 0.9 and 2 equivalents with respect to the quantity of sulphide amide taken as 1 equivalent. The solvent used was ethyl acetate.

TABLE 14

| Entry | CuOOH/ sulphide amide | Ee % | Purity % | Sulphone amide % | Sulphide amide % | Yield % |
|---|---|---|---|---|---|---|
| 1 | 0.9/1 | 99.2 | 98.88 | 0.08 | 0.91 | 72.8 |
| 2 | 1/1 | 99.6 | 99.88 | 0.02 | 0.10 | 72 |
| 3 | 1.1/1 | 99.6 | 99.87 | 0.13 | <DL | 77.5 |
| 4 | 2/1 | 99.5 | 99.29 | 0.70 | <DL | 67.8 |

E.e. = enantiomeric excess; CuOOH = cumene hydroperoxide; DL = detection limit

Results reported in table 14 showed that the enantioselectivity of the reaction was high, being equal or superior to 99.2%. The purity was high as well, being, in particular, equal to 99.87% when 1 and 1.1 equivalent of oxidant with respect to the sulphide amide (1 equivalent) were added in the reaction mixture. For 1 equivalent of oxidant, the percentage of sulphone detected was as low as 0.02%. The amount of sulphide was below the detection limit for 1.1 to 2 equivalents of oxidant.

Example 14

Influence of the Quantity of Chiral Ligand on the Enantioselectivity and the Purity of the Asymmetric Oxidation In the general experimental protocol defined above, the quantity of chiral ligand [(S,S)-(−)diethyl tartrate] was varied between 1 and 2 equivalents with respect to the quantity of titanium isopropoxide taken as 1 equivalent in the chiral ligand titanium complex. The solvent used was ethyl acetate.

TABLE 15

| Entry | DET/Ti/H$_2$O | E.e. (%) | Purity (%) | Yield (%) |
|---|---|---|---|---|
| 1 | 2/1/0.5 | 99.4 | 99.7 | 71.4 |
| 2 | 1.5/1/0.5 | 94.8 | 99.7 | 76.9 |
| 3 | 1/1/0.5 | 69.4 | — | — |

E.e. = enantiomeric excess;
DET = [(S,S)-(−)diethyl tartrate;
Ti = titaniumisopropoxide;
— = not determined An enantioselectivity close to 95% or higher than 99% and a purity superior to 99% were obtained for a chiral ligand titanium complex stoichiometry in the 1.5/1/0.5-2/1/0.5 range.

Example 15

Reproducibility of the Asymmetric Oxidation Reaction

The reproducibility of the asymmetric oxidation reaction of the diphenylmethyl-thioacetamide as defined in the general protocol above was assessed repeatedly in four separate experiments in ethyl acetate used as solvent.

TABLE 16

| Entry | E.e. (%) | Purity (%) | Sulphide amide (%) | Sulphone amide (%) | Yield (%) |
|---|---|---|---|---|---|
| 1 | 99.6 | 99.84 | 0.10 | 0.05 | 73.3 |
| 2 | 99.6 | 99.86 | 0.05 | 0.09 | 74 |
| 3 | 99.6 | 99.79 | 0.13 | 0.05 | 73.9 |
| 4 | 99.6 | 99.88 | 0.10 | 0.02 | 72 |

E.e. = enantiomeric excess

As shown in table 16, the reproducibility of the results is high. The enantioselectivity was repeatedly found superior or equal to 99.6% and the purity superior or equal to 99.8%. The levels of impurities were very low with only measurable levels of the sulphone amide in the 0.02-0.09% range and of the remaining parent compound sulphide amide in the 0.05-0.13% range. Search for other impurities as for example the corresponding sulphide acid or ester or their sulphone derivatives was unsuccessful.

Example 16

Influence of the Structure of Pro-Chiral Sulphide Derivatives on the Enantioselectivity and the Purity of the Asymmetric Oxidation The following pro-chiral sulphide derivatives were assayed in the experimental conditions as defined in the general procedure above and ethyl acetate as solvent.

TABLE 17

| | Pro-chiral sulphide derivatives | | | | | | E.e. % | Conversion rate (%) |
|---|---|---|---|---|---|---|---|---|
| Entry | R1a | R1 | R2a | R2 | n | Y | | |
| 1 | H | H | H | H | 1 | CONH$_2$ | 99.6 | ~100 |
| 2 | 4-F | 4'-F | H | H | 1 | CONH$_2$ | 92.5 | 99 |
| 3 | H | H | H | H | 1 | CONHCH$_3$ | 96.4 | ~97 |
| 4 | H | H | H | H | 1 | CONHCH$_2$Ph | ~93 | ~97 |
| 5 | H | H | H | H | 1 | CN | ~92 | ~94 |

Results indicated that the protocol may be applied to the compounds, giving a good enantioselectivity as high as 92%-99.6% in most cases and a good conversion rate in the 94%-100% range. In addition a crystallization step may be applied to the isolated end product of the reaction in order to increase the enantiomeric conversion and/or the purity of the desired enantiomer.

Example 17

Example 17 corresponds to the comparative Examples 1 to 3. The general procedure used to prepare sulphoxides was as described above:

General Procedure

Oxidation of sulphide in accordance with the method described by Kagan et al. Organic Syntheses, John Wiley and Sons INC. ed., 1993; vol. VIII, 464-467.

Water (0.27 mL, 0.015 mol, 1.0 eq) was added dropwise at room temperature (20° C.) to a solution of diethyltartrate (DET) (6.19 g, 0.03 mol, 2.0 eq) and titanium (IV) isopropoxide (4.26 g, 4.43 mL, 0.015 mol, 1.0 eq) in 125 mL of anhydrous methylene chloride, under nitrogen. Stirring was maintained until the yellow solution became homogeneous (30 min) and the sulphide (0.03 mol, 2.0 eq) was added. The solution was cooled to −30° C. and left in contact for 50 minutes at −30° C. Then, cumene hydroperoxide (4.57 g, 5.0 mL, 0.03 mol, 2.0 eq) was added and the mixture was kept at −25° C. for 15 hours. After this time, 5 mL of water were added, and the solution was stirred during 1 h 30. The medium was filtered on clarcel and the filtrate worked up depending on the sulphoxide obtained. As an example, when the sulphoxide of diphenylmethylthioacetic acid was generated, the compound was extracted with 3×100 mL of an aqueous solution of K$_2$CO$_3$ (0.6 M). The aqueous phases were collected, filtered on clarcel, acidified by addition of 150 mL of an aqueous solution of chlorhydric acid 4N (pH≈1). The precipitate formed is filtered on a fritted glass, rinsed with water and then dried in vacuo at 35° C.

Comparative Example 1

Enantioselectivity of Asymmetric Oxidation of Sulphides of Formula (II) with n=1 According to X=—NH$_2$, —OCH$_3$, —OH The above general procedure for comparative examples was applied to diphenylmethylthioacetamide, methyldiphenylmethylthioacetate or diphenylmethyl-thioacetic acid as sulphide, and by using either (R,R)-DET or (S,S)-DET.

TABLE 18

| Precursor | DET | Ee % | Conversion rate (%) |
|---|---|---|---|
| Diphenylmethylthioacetamide | (R,R)-(+)-DET | 42 | 90 |
| Methyldiphenylmethylthioacetate | (R,R)-(+)-DET | 10 | 40 |
| Diphenylmethylthioacetic acid | (R,R)-(+)-DET | 50 | 70 |
| Diphenylmethylthioacetic acid | (S,S)-(−)-DET | 50 | 83 |

Comparative Example 2

Influence of the Amount of Oxidizing Agent on the Enantioselectivity of Oxidation of Diphenylmethylthioacetic Acid The above general procedure for comparative examples was applied to diphenylmethylthioacetic acid by varying the amount of cumene hydroperoxide from 1 to 4 equivalents.

TABLE 19

| Cumene Hydroperoxide (eq) | Ee (%) | Conversion rate (%) |
|---|---|---|
| 1 | 50 | 83 |
| 2 | 50 | 92 |
| 4 | 50 | 97 |

The increase of the amount of the oxidizing agent allows to enhance the conversion rate of sulphide into sulphoxide but does not improve the enantioselectivity of the reaction, according to the Kagan's procedure.

Comparative Example 3

Influence of the Stoichiometry of the Titanium Chiral Complex on the Enantioselectivity of Oxidation of Diphenylmethylthioacetic Acid The above general procedure for comparative examples was applied to diphenylmethylthioacetic acid by varying the stoichiometry of the chiral titanium complex (S,S)-(−)-DET/Ti/$H_2O$.

TABLE 20

| (S,S)-(−)-DET/Ti/$H_2O$ | Ee (%) | Conversion rate (%) |
|---|---|---|
| 2/1/1 | 50 | 92 |
| 2/1/0 | 0 | 97 |
| 4/1/0 | 0 | 97 |

The water is necessary to obtain an enantioselectivity, according to the Kagan's procedure.

Examples 18 to 24

Examples 18 to 23 correspond to examples of optional re-worked processes that may be applied to the crystallized end product resulting from the asymmetric oxidation and isolated by filtration in order either to obtain:
   an enantiomerically enriched form of the targeted enantiomer,
   a specific polymorphic form of the enantiomer,
and/or
   to achieve a higher degree of purity by removing impurities as, as example, the initial pro-chiral sulphide and/or the suphone.

As used hereafter, the forms I, II and IV refer to the polymorphic forms of (−)-modafinil disclosed in WO 2004/060858.

Example 18

A suspension of (−)-modafinil enantiomerically enriched (5 g; 0.018 mole) and ethanol 95% (20 to 25 mL; 4 to 5 volumes) was reflux under stirring for 5 minutes. The solution obtained was cooled first to room temperature (25° C.) and then kept at 4° C. for 1 or 2 hours. The crystallized sulphoxide was filtered under vacuum, washed with cold ethanol (95%) and dried under vacuum in an oven at 40° C. Results are reported in table 21.

TABLE 21

| | Initial | | | Final | | |
|---|---|---|---|---|---|---|
| Entry | E.e. (%) | Purity (%) | Polymorphic Form | E.e. (%) | Purity (%) | Polymorphic Form |
| 1 | 93.0 | — | — | 98.6 | — | — |
| 2 | 91.6 | — | — | 99.1 | — | — |
| 3 | 94.0 | — | — | 98.4 | 99.5 | I |
| 4 | 98.8 | 99.4 | II | 99.0 | 99.6 | I |
| 5 | 95.4 | 99.9 | — | 97.2 | 99.8 | I |
| 6 | 96.8 | 99.5 | I | 98.0 | 99.7 | I |

E.e. = enantiomeric excess; —: not determined

As shown in table 21, the enantiomeric excess was increased by crystallization in an ethanol/$H_2O$ (95/5) mixture. Such treatments lead to (−)-modafinil polymorphic form I.

Example 19

Crystallization of (−)-modafinil enantiomerically enriched was performed in Tetrahydrofuran/$H_2O$ (95/5) and acetone/$H_2O$ (95/5) mixtures according to the experimental conditions described in Example 18.

TABLE 22

| | | Initial | | | Final | | |
|---|---|---|---|---|---|---|---|
| Entry | Solvent | E.e. (%) | Sulphide amide (%) | Sulphone amide (%) | E.e. (%) | Sulphide amide (%) | Sulphone amide (%) |
| 1 | THF/$H_2O$ (95/5) | 94.2 | 1.10 | 1.90 | 99.8 | ND | 0.40 |
| 2 | THF/$H_2O$ (95/5) | 94.8 | 0.12 | 0.11 | 99.4 | ND | 0.10 |
| 3 | Acetone/$H_2O$ (95/5) | 94.8 | 0.06 | 0.24 | 98.2 | ND | 0.30 |

E.e. = enantiomeric excess; ND: not detectable

Results reported in table 22 show an increase of the enantiomeric excess as well as a decrease of the pro-chiral sulphide amide below the detection limit. The quantity of sulphone amide was decreased as well.

Example 20

A suspension of (−)-modafinil enantiomerically enriched (12.15 g; 0.044 moles) and THF (122 mL) was slowly heated under stirring until dissolution is complete and then refluxed. The solution was cooled at a controlled rate of −0.5° C./min to 0° C. and kept at this temperature for 45 minutes. The crystallized sulphoxide was filtered and dried at 40° C. under vacuum. Results are reported in table 23.
   Yield: 77.1%

TABLE 23

| Initial | | | | Final | | | |
|---|---|---|---|---|---|---|---|
| E.e. (%) | Purity (%) | Sulphone amide (%) | Sulphide amide (%) | E.e. (%) | Purity (%) | Sulphone amide (%) | Sulphide amide (%) |
| 99.2 | 98.50 | 0.25 | 0.28 | 100 | 99.71 | 0.05 | 0.01 |

E.e. = enantiomeric excess

In the above described experimental conditions, the added crystallization step increased the enantiomeric excess and the global percent of purity, while decreasing the levels of sulphone formed as well as the remaining untreated pro-chiral sulphide amide levels.

Example 21

To a 250 mL flask containing 180 mL of dichloromethane, (−)-modafinil enantiomerically enriched (10 g; 0.036 mole) form II was added. The mixture was heated to reflux and stirred until a solution was obtained. 125 mL of solvent were condensed in a dean-stark extension. The remaining suspension was cooled to room temperature and then placed in an ice-water bath for 1 hour. The crystallized sulphoxide was filtered off and dried at 40° C. under vacuum.

Yield: 84.6%.

TABLE 24

| Initial | | | | Final | | | |
| --- | --- | --- | --- | --- | --- | --- | --- |
| E.e. (%) | Purity (%) | Sulphone amide (%) | Sulphide amide (%) | E.e. (%) | Purity (%) | Sulphone amide (%) | Sulphide amide (%) |
| 99.2 | 98.50 | 0.25 | 0.28 | 100 | 99.71 | 0.03 | 0.02 |

E.e. = enantiomeric excess

In the above described experimental conditions, the crystallization step increased the purity level. The sulphone amide and the pro-chiral sulphide amide levels were decreased after this additional treatment. The final sulphoxide was crystallized as the polymorphic form IV.

Example 22

A suspension of (−)-modafinil enantiomerically enriched (10 g; 0.036 mole) in acetonitrile (100 mL) was heated up to reflux under stirring (350 rpm) until complete dissolution. Then, the solution was cooled to 0° C. at a rate of −0.5° C./min and stirred (350 rpm) for about 1 hour. The crystallized sulphoxide was filtered off and dried at 40° C. under vacuum.

Yield: 69.3%.

TABLE 25

| Initial | | | | Final | | | |
| --- | --- | --- | --- | --- | --- | --- | --- |
| E.e. (%) | Purity (%) | Sulphone amide (%) | Sulphide amide (%) | E.e. (%) | Purity (%) | Sulphone amide (%) | Sulphide amide (%) |
| 99.2 | 98.50 | 0.25 | 0.28 | 100 | 99.90 | 0.02 | 0.03 |

E.e. = enantiomeric excess

The (−)-diphenymethylsulphinylacetamide was obtained with a 100% enantiomeric excess and the sulphone amide and the pro-chiral sulphide amide levels were decreased after the additional crystallization treatment.

Example 23

A suspension of (−)-modafinil enantiomerically enriched (10 g; 0.036 mole) in ethyl acetate (150 mL) was heated to reflux under stirring (350 rpm). Then methanol (25 mL) was added to achieve complete dissolution. Then, the solution was cooled to 0° C. at a rate of −0.5° C./min and stirred (350 rpm) for 45 minutes. The crystallized sulphoxide was filtered off and dried at 40° C. under vacuum.

Yield: 38%.

TABLE 26

| Initial | | | | Final | | | |
| --- | --- | --- | --- | --- | --- | --- | --- |
| E.e. (%) | Purity (%) | Sulphone amide (%) | Sulphide amide (%) | E.e. (%) | Purity (%) | Sulphone amide (%) | Sulphide amide (%) |
| 99.2 | 98.50 | 0.25 | 0.28 | 99.8 | 99.54 | 0.04 | 0.03 |

E.e. = enantiomeric excess

As reported in table 26, the crystallization step in ethyl acetate and methanol mixture decreased the sulphone amide and the pro-chiral sulphide amide levels by 84 and 89%, respectively.

Example 24

Synthesis of the Diphenylmethylthioacetamide

A reactor equipped with an impeller stirrer and a gas introduction tube was charged with methyldiphenylmethylthioacetate (100 g; 1 equivalent) and methanol (300 mL; 3 volumes) at room temperature. The mixture was heated to 35° C. Ammonia (7 equivalents) was introduced within 3 hours, and the mixture contacted at 35° C. for 16 hours before adding 3 equivalents of ammonia. When the reaction was completed, the mixture was cooled to 25° C. and water (90 ml; 0.9 volume) added. The mixture was filtered and dried under vacuum.
Yield: 83%
$^1$H-NMR (CDCl$_3$, 400 MHz): δ H 7.41 (d, 4H, H arom), 7.32 (t, 4H, H arom), 7.25 (t, 2H, H arom), 6.53 (s, 1H, NH$_2$), 6.22 (s, 1H, NH$_2$), 5.18 (s, 1H, CH), 3.07 (s, 2H, CH$_2$).

Example 25

Asymmetric Synthesis of methyl(−)-2-[(diphenyl)methylsulfiny]acetate

General Procedure

In a 100 mL vessel (AutoMATE-HEL), methyldiphenylmethylthioacetate (5 g; 18.4 mmol; 1.0 eq) was dissolved in toluene (20 mL; 4 vol.). To the solution were added (R,R)-(+)-diethyl-tartrate (1.9 mL; 11.0 mmol; 0.6 eq) and titanium (IV) tetraisopropoxide (1.7 mL; 5.5 mmol; 0.3 eq) at 54° C. In these conditions, the resulting chiral titanium complex had the stoichiometry: DET/Ti(OiPr)$_4$:2/1 and corresponded to 0.3 eq with respect to methyldiphenylmethylthioacetate under stirring. Stirring was maintained at 54° C. during at least 60 minutes.

After cooling to room temperature (30° C.), triethylamine (1.6 mL; 11.0 mmol; 0.6 eq) was added to the mixture and contacted for 20 minutes. Then, cumene hydroperoxide (3.4 mL; 18.4 mmol; 1.0 eq) was slowly added within 6 to 11 minutes. The formation of the reaction end product methyl (−)-2-(diphenyl-methylsulfinyl)acetate was assessed over a 24 hours period. The enantiomeric excess was measured repeatedly by HPLC (refer to material and method section).

All the following experiments were performed in accordance with the conditions of the general procedure, by modifying parameters as indicated in table 27.

TABLE 27

| Entry | General Protocol modifications | E.e. (%) | Conversion rate (%) |
|---|---|---|---|
| 1 | — | 83.5 | 87.9 |
| 2 | Triethylamine (2.6 mL; 1 eq) | 83.2 | 83.2 |
| 3 | Triethylamine (3.9 mL; 1.5 eq) | 84.1 | 71.4 |
| 4 | Cumene hydroperoxide (4 mL; 1.2 eq) | 81.3 | 87.5 |
| 5 | Oxidation reaction temperature: 35° C. | 73.8 | 77.3 |

As shown in table 27, the methyl(−)-2-(diphenylmethylsulfinyl)acetate was formed with a high enantioselectivity, superior to 81%, and a high conversion rate in the above conditions.

We claim:
1. A three-step method for preparing (R)-modafinil having an enantiomeric excess of at least about 99.0%, wherein the steps comprise:
   a. dissolving (R)-modafinil having an enantiomeric excess of about 91.6% to about 98.8% in a solvent to form a solution;
   b. crystallizing (R)-modafinil from the solution; and
   c. isolating the crystallized (R)-modafinil, wherein the isolated (R)-modafinil has an enantiomeric excess of at least about 99.0%.
2. The method of claim 1, wherein the solvent comprises ethanol, tetrahydrofuran, acetone, dichloromethane, acetonitrile, or ethyl acetate.
3. The method of claim 2, wherein the solvent comprises ethanol.
4. The method of claim 2, wherein the solvent comprises tetrahydrofuran, acetone, dichloromethane, acetonitrile, or ethyl acetate.
5. The method of claim 4, wherein the solvent comprises tetrahydrofuran.
6. The method of claim 5, wherein the solvent comprises a mixture of tetrahydrofuran and water.
7. The method of claim 6, wherein the solvent comprises a mixture of about 95/5 tetrahydrofuran/water.
8. The method of claim 4, wherein the solvent comprises dichloromethane.
9. The method of claim 4, wherein the solvent comprises acetonitrile.
10. The method of claim 4, wherein the solvent comprises ethyl acetate.
11. The method of claim 10, wherein the solvent comprises a mixture of ethyl acetate and methanol.
12. The method of claim 11, wherein the solvent comprises a mixture of about 6/1 ethyl acetate/methanol.
13. The method of claim 4, wherein the solvent comprises acetone.
14. The method of claim 13, wherein the solvent comprises a mixture of acetone and water.
15. The method of claim 14, wherein the solvent comprises a mixture of about 95/5 acetone/water.
16. The method of claim 1, wherein the crystallized (R)-modafinil is isolated by filtration.
17. The method of claim 1, wherein the isolated (R)-modafinil has an enantiomeric excess of at least about 99.5%.
18. The method of claim 1, wherein the isolated (R)-modafinil has an enantiomeric excess of at least about 99.8%.
19. The method of claim 4, wherein the isolated (R)-modafinil has an enantiomeric excess of at least about 99.5%.
20. The method of claim 4, wherein the isolated (R)-modafinil has an enantiomeric excess of at least about 99.8%.
21. The method of claim 1, wherein the (R)-modafinil in step (a) has an enantiomeric excess of less than about 98%.
22. The method of claim 1, wherein the (R)-modafinil in step (a) has an enantiomeric excess of less than about 97%.
23. The method of claim 1, wherein the (R)-modafinil in step (a) has an enantiomeric excess of less than about 96%.
24. The method of claim 1, wherein the (R)-modafinil in step (a) has an enantiomeric excess of less than about 95%.
25. The method of claim 2, wherein the (R)-modafinil in step (a) has an enantiomeric excess of less than about 98%.
26. The method of claim 2, wherein the (R)-modafinil in step (a) has an enantiomeric excess of less than about 97%.
27. The method of claim 2, wherein the (R)-modafinil in step (a) has an enantiomeric excess of less than about 96%.
28. The method of claim 2, wherein the (R)-modafinil in step (a) has an enantiomeric excess of less than about 95%.

29. The method of claim 3, wherein the (R)-modafinil in step (a) has an enantiomeric excess of less than about 98%.

30. The method of claim 3, wherein the (R)-modafinil in step (a) has an enantiomeric excess of less than about 97%.

31. The method of claim 3, wherein the (R)-modafinil in step (a) has an enantiomeric excess of less than about 96%.

32. The method of claim 3, wherein the (R)-modafinil in step (a) has an enantiomeric excess of less than about 95%.

33. The method of claim 4, wherein the (R)-modafinil in step (a) has an enantiomeric excess of less than about 98%.

34. The method of claim 4, wherein the (R)-modafinil in step (a) has an enantiomeric excess of less than about 97%.

35. The method of claim 4, wherein the (R)-modafinil in step (a) has an enantiomeric excess of less than about 96%.

36. The method of claim 4, wherein the (R)-modafinil in step (a) has an enantiomeric excess of less than about 95%.

37. The method of claim 1, further comprising the step of recrystallizing the isolated crystallized (R)-modafinil.

38. The method of claim 2, further comprising the step of recrystallizing the isolated crystallized (R)-modafinil.

* * * * *